(12) United States Patent
Stephan et al.

(10) Patent No.: US 10,395,912 B2
(45) Date of Patent: Aug. 27, 2019

(54) SPRAY CHAMBERS AND METHODS OF USING THEM

(71) Applicant: PERKINELMER HEALTH SCIENCES CANADA, INC., Woodbridge (CA)

(72) Inventors: Chady Stephan, Brampton (CA); Hamid Badiei, Woodbridge (CA); Serguei Savtchenko, Woodbridge (CA); Samad Bazargan, York (CA)

(73) Assignee: PerkinElmer Health Sciences Canada, Inc., Woodbridge (ON) (CA)

( * ) Notice: Subject to any disclaimer, the term of this patent is extended or adjusted under 35 U.S.C. 154(b) by 0 days.

(21) Appl. No.: 16/146,752

(22) Filed: Sep. 28, 2018

(65) Prior Publication Data

US 2019/0189416 A1  Jun. 20, 2019

Related U.S. Application Data

(63) Continuation of application No. 15/597,608, filed on May 17, 2017, now Pat. No. 10,147,592.

(60) Provisional application No. 62/337,997, filed on May 18, 2016.

(51) Int. Cl.
| | |
|---|---|
| *H01J 49/00* | (2006.01) |
| *H01J 49/10* | (2006.01) |
| *H01J 49/04* | (2006.01) |
| *H01J 49/16* | (2006.01) |
| *G01N 30/72* | (2006.01) |

(52) U.S. Cl.
CPC ........ *H01J 49/107* (2013.01); *G01N 30/7273* (2013.01); *H01J 49/045* (2013.01); *H01J 49/049* (2013.01); *H01J 49/167* (2013.01)

(58) Field of Classification Search
CPC .. H01J 49/00; H01J 49/02; H01J 49/10; H01J 49/107; H01J 49/16; H01J 49/165; H01J 49/167; H01J 49/102; H01J 49/12; H01J 49/168
USPC ........................................ 250/281, 282, 288
See application file for complete search history.

(56) References Cited

U.S. PATENT DOCUMENTS

| | | | | |
|---|---|---|---|---|
| 4,958,529 A | * | 9/1990 | Vestal ................ | G01N 30/7273 250/288 |
| 5,868,322 A | * | 2/1999 | Loucks, Jr. ........... | B05B 5/0255 239/418 |
| 2011/0248003 A1 | * | 10/2011 | Wiederin ................. | H05H 1/30 219/121.51 |

* cited by examiner

*Primary Examiner* — Jason L McCormack
(74) *Attorney, Agent, or Firm* — Rhodes IP PLC; Christopher R Rhodes

(57) ABSTRACT

Devices, systems and methods including a spray chamber are described. In certain examples, the spray chamber may be configured with an outer chamber configured to provide tangential gas flows. In other instances, an inner tube can be positioned within the outer chamber and may comprise a plurality of microchannels. In some examples, the outer chamber may comprise dual gas inlet ports. In some instances, the spray chamber may be configured to provide tangential gas flow and laminar gas flows to prevent droplet formation on surfaces of the spray chamber. Optical emission devices, optical absorption devices and mass spectrometers using the spray chamber are also described.

15 Claims, 32 Drawing Sheets

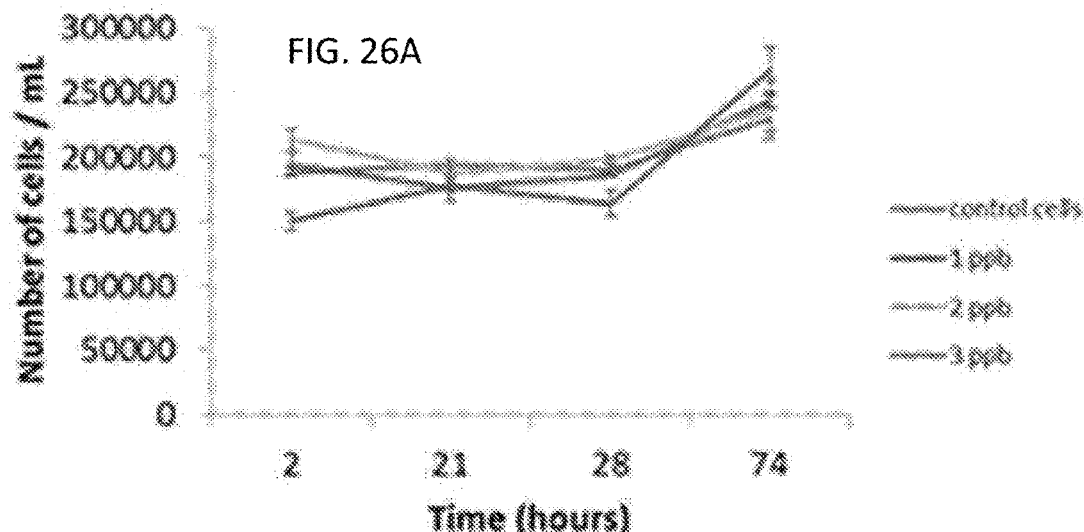
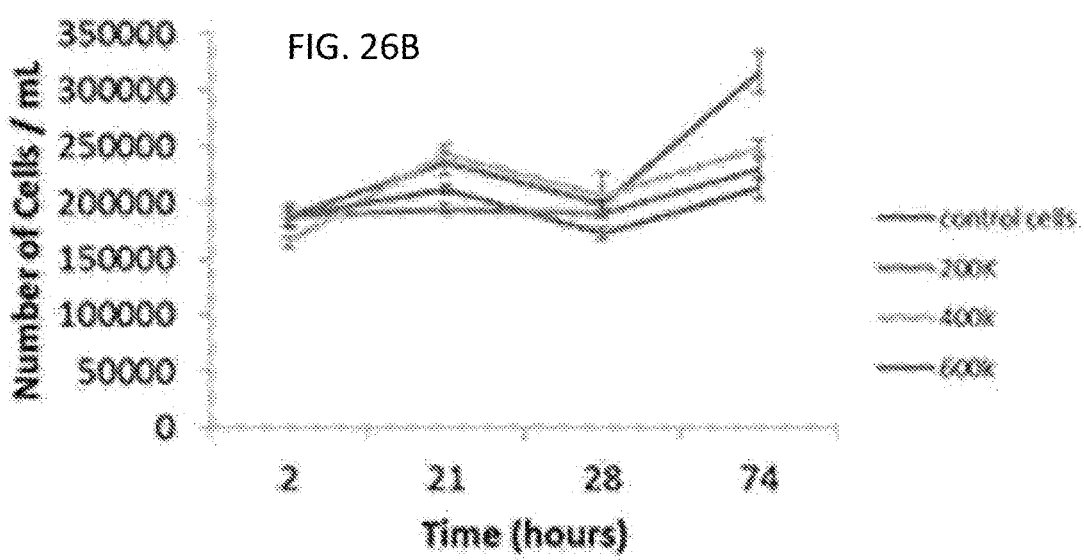

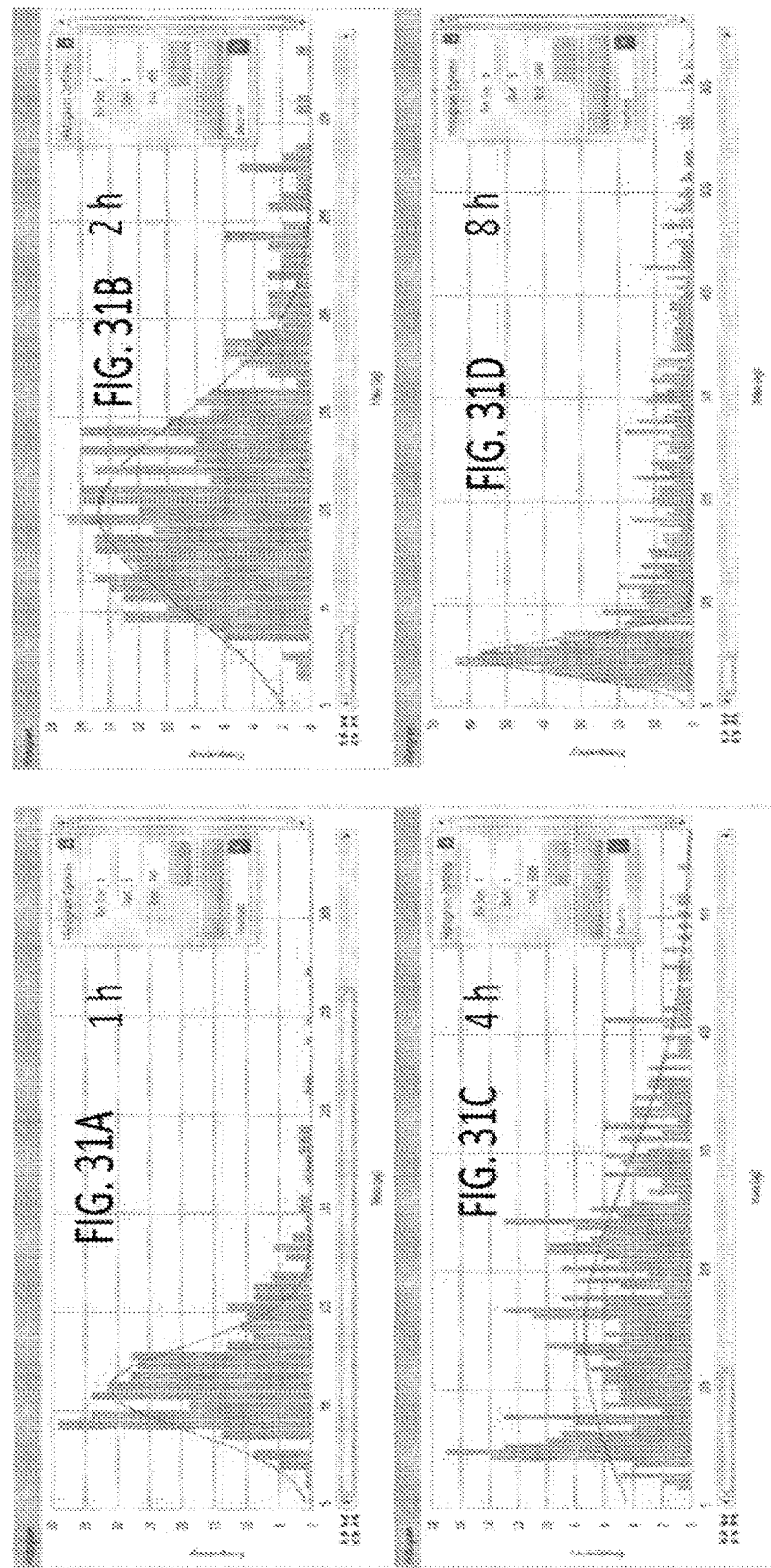

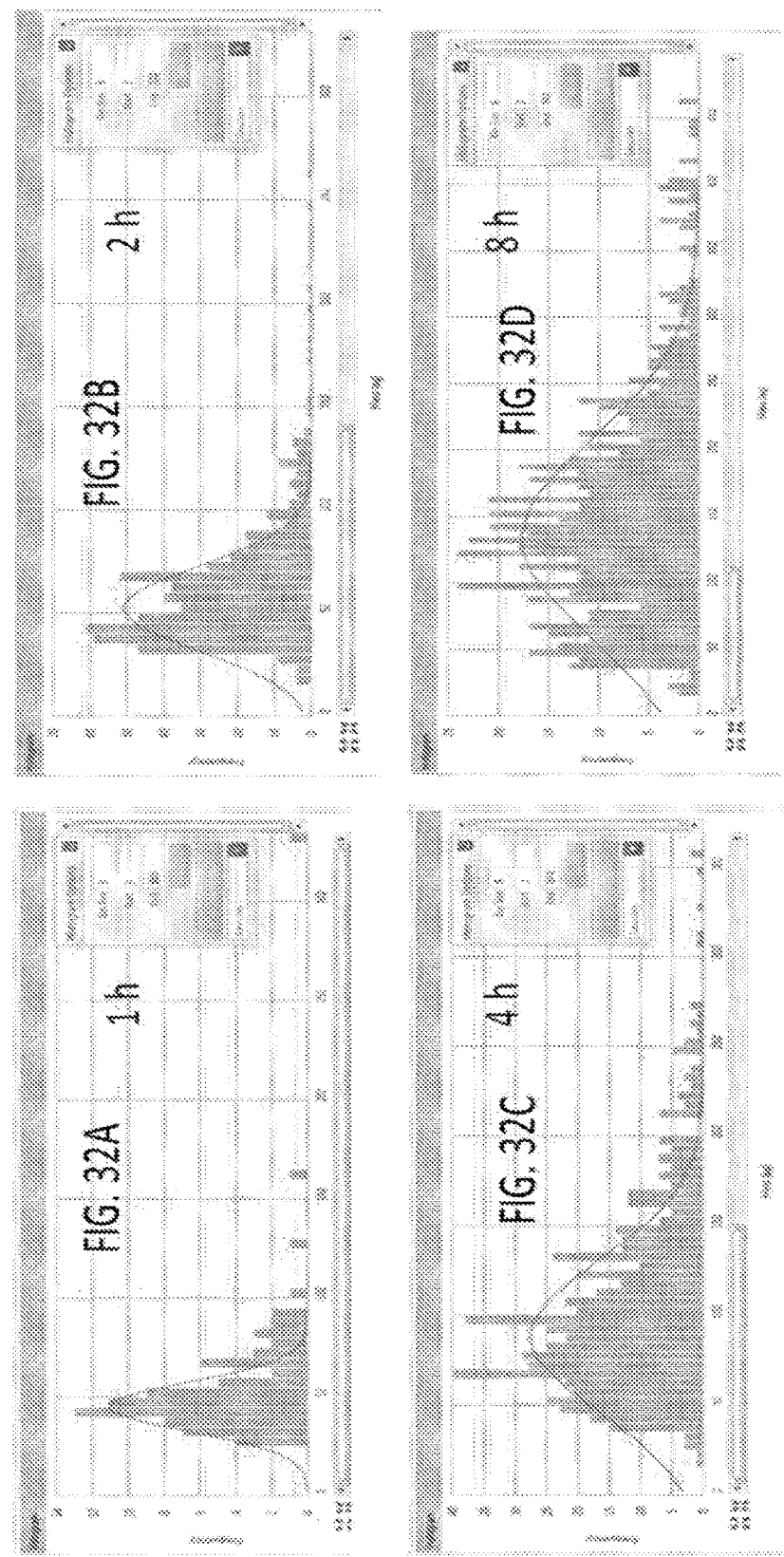

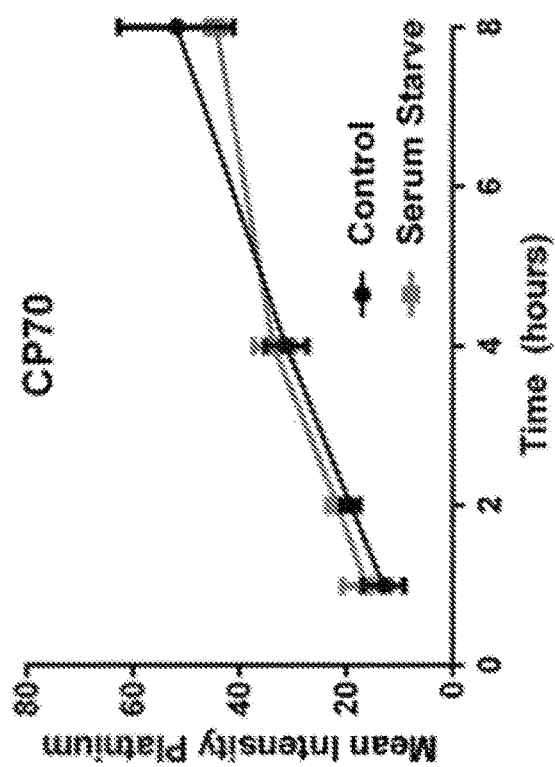
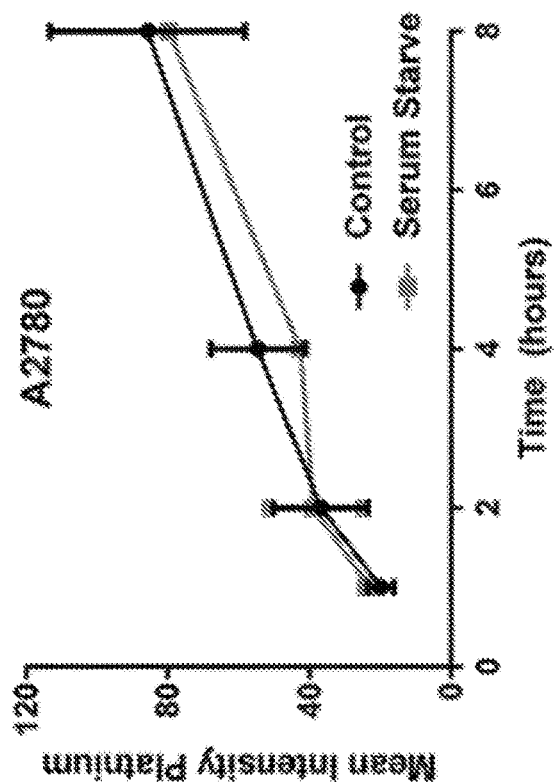
FIG. 34B
FIG. 34A

SPRAY CHAMBERS AND METHODS OF USING THEM

PRIORITY APPLICATION

This application is related to, and claims priority to and the benefit of, U.S. Provisional Application No. 62/337,997 filed on May 18, 2016, the entire disclosure of which is hereby incorporated herein by reference for all purposes.

TECHNOLOGICAL FIELD

Certain examples disclosed herein relate to spray chambers and their use in single molecule or single cell analyses. More particularly, certain examples described herein are directed to spray chambers and their use to introduce a sample into a plasma or other ionization source or ionization device.

BACKGROUND

A plasma may be used to ionize and/or atomize a sample. A liquid sample is typically provided to the plasma in the form of an aerosol by way of one or more sample introduction devices.

SUMMARY

Certain aspects, examples, embodiments, and configurations of spray chambers are described in more detail below to illustrate some of the many different forms of a spray chamber suitable for use with an ionization device or source.

In a first aspect, a spray chamber configured to couple to a nebulizer at an inlet end to receive a liquid sample from the nebulizer and provide an aerosolized sample spray at an outlet end to an ionization device is provided. In some configurations, the spray chamber comprises an outer chamber comprising the inlet end, the outlet end and dual makeup gas inlet ports each configured to receive a gas to provide a tangential gas flow within the outer chamber, and an inner tube within the outer chamber, the inner chamber comprising a plurality of internal microchannels configured to receive makeup gas introduced into the outer chamber from the dual makeup gas inlets, in which the inner tube is sized and arranged to provide a laminar flow between an outer surface of the inner tube and an inner surface of the outer chamber to reduce droplet deposition on the inner tube.

In certain examples, at least one microchannel of the plurality of microchannels is positioned to prevent backflow of the received liquid sample. In some embodiments, the outer chamber comprises rounded edges at the inlet end to promote the laminar flow. In other examples, the dual makeup gas inlets are positioned in a same radial plane. In some instances, the outer chamber further comprises a drain port. In other examples, the inner tube comprises a cone shape. In some examples, an inner diameter of the outer chamber is smaller at the outlet end than at the inlet end. In additional examples, the dual makeup gas inlets are positioned adjacent to the inlet end of the outer chamber. In other examples, the dual makeup gas inlets are positioned adjacent to the outlet end of the outer chamber. In some examples, an inner diameter of the inner tube increases in a longitudinal direction from the inlet end toward the outlet end of the outer chamber. In some embodiments, an inner diameter of the inner tube decreases in a longitudinal direction from the inlet end toward the outlet end of the outer chamber.

In certain configurations, the outer chamber comprises the dual makeup gas inlets adjacent to the inlet end, an inner diameter of the inner tube increases in a longitudinal direction from the inlet end toward the outlet end of the outer chamber, and an inner diameter of the outer chamber is smaller at the outlet end than at the inlet end.

In other configurations, the outer chamber comprises the dual makeup gas inlets adjacent to the inlet end, an inner diameter of the inner tube is substantially constant in a longitudinal direction, and an inner diameter of the outer chamber is smaller at the outlet end than at the inlet end.

In some configurations, the outer chamber comprises the dual makeup gas inlets adjacent to the outlet end, an inner diameter of the inner tube is smaller at the outlet end of the outer chamber than at the inlet end of the outer chamber, and an inner diameter of the outer chamber is substantially constant from the inlet end to the outlet end.

In some examples, the outer chamber comprises internal rounded edges at the inlet end.

In another aspect, a spray chamber can be configured to fluidically couple to a liquid sample delivery device at an inlet end and to select and spray a single particle or cell at an outlet end to a ionization device fluidically coupled to the spray chamber. In some embodiments, the spray chamber comprises an outer chamber comprising dual gas inlet ports each configured to fluidically couple to a makeup gas source configured to provide a makeup gas to provide tangential gas flow within the outer chamber. In some examples, the spray chamber further comprises an inner tube within and coupled to the outer chamber. In some instances, the inner tube comprises a plurality of microchannels each configured to receive the makeup gas to prevent droplets of the liquid sample from depositing on surfaces of the inner tube. In some configurations, the inner tube is positioned to provide a laminar flow within the outer chamber to prevent droplet formation on inner surfaces of the outer chamber.

In certain examples, at least one microchannel of the plurality of microchannels is positioned to prevent backflow of the liquid sample in the outer chamber. In other examples, the outer chamber comprises rounded edges at the inlet end to promote the laminar flow. In some examples, the dual gas inlets are positioned in a same radial plane. In some embodiments, the outer chamber further comprises a drain port. In certain examples, the inner tube comprises a cone shape. In some configurations, an inner diameter of the outer chamber is smaller at the outlet end than at the inlet end. In other configurations, the dual gas inlets are positioned adjacent to the inlet end of the outer chamber. In certain examples, the dual gas inlets are positioned adjacent to the outlet end of the outer chamber. In some embodiments, an inner diameter of the inner tube increases in a longitudinal direction from the inlet end toward the outlet end of the outer chamber. In other embodiments, an inner diameter of the inner tube decreases in a longitudinal direction from the inlet end toward the outlet end of the outer chamber.

In certain examples, the outer chamber comprises the dual gas inlets adjacent to the inlet end, an inner diameter of the inner tube increases in a longitudinal direction from the inlet end toward the outlet end of the outer chamber, and an inner diameter of the outer chamber is smaller at the outlet end than at the inlet end.

In other configurations, the outer chamber comprises the dual gas inlets adjacent to the inlet end, an inner diameter of the inner tube is substantially constant in a longitudinal direction, and an inner diameter of the outer chamber is smaller at the outlet end than at the inlet end.

In some configurations, the outer chamber comprises the dual gas inlets adjacent to the outlet end, an inner diameter of the inner tube is smaller at the outlet end of the outer chamber than at the inlet end of the outer chamber, and an inner diameter of the outer chamber is substantially constant from the inlet end to the outlet end.

In certain examples, the outer chamber comprises internal rounded edges at the inlet end.

In an additional aspect, a spray chamber comprises an outer chamber comprising dual gas inlet ports each configured to fluidically couple to a makeup gas source configured to provide a makeup gas to provide tangential gas flow within the outer chamber. For example, the spray chamber can be configured to fluidically couple to a liquid sample delivery device at an inlet end and to spray an aerosolized analyte at an outlet end to a ionization device fluidically coupled to the spray chamber. In some instances, the dual gas inlet ports are positioned in different longitudinal planes to assist in providing the tangential gas flows within the outer chamber.

In certain configurations, the outer chamber comprises rounded edges at the inlet end to promote the laminar flow. In other configurations, the outer chamber further comprises a drain port. In some examples, the dual gas inlets are positioned adjacent to the inlet end of the outer chamber or the dual gas inlets are positioned adjacent to the outlet end of the outer chamber. In some embodiments, an outer diameter of the outer chamber is substantially constant in a longitudinal direction. In other examples, the spray chamber comprises an inner tube positioned within the outer chamber, wherein the inner tube comprises a plurality of microchannels each configured to receive the makeup gas to prevent droplets of the liquid sample from depositing on surfaces of the inner tube, wherein the inner tube is positioned to provide a laminar flow within the outer chamber to prevent droplet formation on inner surfaces of the outer chamber.

In another aspect, a method of analyzing inorganic or organic species in single cells in a cell population comprises introducing a cell population into a spray chamber as described herein, selecting a single cell from the introduced cell population, spraying the selected single cell into an ionization device to analyze the inorganic or organic species in the selected single cell, and detecting at least one inorganic or organic species in the sprayed, selected single cell.

In certain examples, the method comprises selecting the cell population to be a mammalian cell derived from endoderm, ectoderm or mesoderm. In some embodiments, the method comprises detecting at least one metal species in the selected, single cell. In certain examples, the method comprises detecting at least one protein in the selected, single cell. In other examples, the method comprises detecting at least one lipid in the selected, single cell. In certain embodiments, the method comprises detecting at least one carbohydrate in the selected, single cell. In other embodiments, the method comprises detecting at least one nucleic acid in the selected, single cell. In some examples, the method comprises detecting a level of an external agent taken up by the selected single cell. In certain instances, the method comprises configuring the ionization device to be an inductively coupled plasma. In other examples, the method comprises detecting the inorganic or organic species from the selected, single cell that has been sprayed into the ionization device using a mass spectrometer. In some instances, the method comprises detecting the inorganic or organic species from the selected, single cell that has been sprayed into the ionization device using optical emission spectroscopy. In other examples, the method comprises detecting the inorganic or organic species from the selected, single cell that has been sprayed into the ionization device using atomic absorption spectroscopy. In certain embodiments, the method comprises configuring the ionization device as a torch and an induction coil, a torch and an induction coil comprising a radial fin, or a torch and an at least one flat plate electrode.

In an additional aspect, a method of analyzing inorganic or organic species in a single cell in a cell population comprises providing a spray chamber as described herein, and providing instructions for using the provided spray chamber to select the single cell from the cell population and to detect at least one inorganic or organic species in the selected, single cell using an ionization device.

In certain examples, the method comprises providing instructions for using the spray chamber with an inductively coupled mass spectrometer to detect the at least one inorganic or organic species in the selected, single cell. In some examples, the method comprises providing instructions for using the spray chamber with an inductively coupled optical emission spectrometer to detect the at least one inorganic or organic species in the selected, single cell. In other examples, the method comprises providing instructions for using the spray chamber with an inductively coupled atomic absorption spectrometer to detect the at least one inorganic or organic species in the selected, single cell. In additional examples, the method comprises providing instructions for using a mammalian cell population to select a single mammalian cell.

In another aspect, a mass spectrometer comprising a spray chamber as described herein, an induction device fluidically coupled to the spray chamber, and a mass analyzer fluidically coupled to the induction device is disclosed.

In certain examples, the mass spectrometer comprises a nebulizer fluidically coupled to the spray chamber. In other examples, the mass spectrometer comprises an injector fluidically coupled to the spray chamber. In some examples, the mass spectrometer comprises a detector fluidically coupled to the mass analyzer. In some configurations, the detector comprises an electron multiplier, a Faraday cup, a multi-channel plate or a scintillation plate. In some embodiments, the induction device comprises an aperture configured to receive a portion of a torch to provide radio frequency energy into the received portion to sustain a plasma within the torch. In other embodiments, the induction device comprises an induction coil. In certain examples, the induction device comprises at least one plate. In some embodiments, the induction device comprises an induction coil comprising at least one radial fin. In other configurations, the mass spectrometer comprises a processor configured to measure single ion burst events as a single cell is sprayed into the induction device from the spray chamber.

In an additional aspect, an optical emission spectrometer comprises a spray chamber as described herein, an induction device fluidically coupled to the spray chamber, and a detector configured to detect optical emission of analyte species introduced into the ionization device from the spray chamber.

In some configurations, the optical emission spectrometer comprises a nebulizer fluidically coupled to the spray chamber. In certain examples, the optical emission spectrometer comprises an injector fluidically coupled to the spray chamber. In some examples, the detector is configured to detect axial optical emission from the analyte species introduced into the torch. In some embodiments, the detector comprises a photomultiplier tube. In some examples, the induction device comprises an aperture configured to receive a portion of a torch to provide radio frequency energy into the received portion to sustain a plasma within the torch. In other embodiments, the induction device comprises an induction coil. In some examples, the induction device comprises at least one plate. In certain instances, the induction device comprises an induction coil comprising at least one radial fin. In other examples, the optical emission spectrometer comprises a processor configured to measure single ion burst events as a single cell is sprayed into the induction device from the spray chamber.

In another aspect, an atomic absorption spectrometer comprises a spray chamber as described herein, an induction device fluidically coupled to the spray chamber, a light source configured to provide light to the induction device, and a detector configured to detect absorption of the light provided to the induction device by analyte species introduced into the induction device from the spray chamber.

In certain examples, the atomic absorption spectrometer comprises a nebulizer fluidically coupled to the spray chamber. In other examples, the atomic absorption spectrometer comprises an injector fluidically coupled to the spray chamber. In certain embodiments, the light source is configured to provide the light axially to the torch. In other examples, the detector comprises a photomultiplier tube. In some examples, the induction device comprises an aperture configured to receive a portion of a torch to provide radio frequency energy into the received portion to sustain a plasma within the torch. In certain embodiments, the induction device comprises an induction coil. In some examples, the induction device comprises at least one plate. In certain embodiments, the induction device comprises an induction coil comprising at least one radial fin. In other examples, the atomic absorption spectrometer comprises a processor configured to measure single ion burst events as a single cell is sprayed into the induction device from the spray chamber.

Additional aspects, embodiments, features and examples will be recognized by the person of ordinary skill in the art, given the benefit of this disclosure, and certain aspects and examples are described in more detail below.

BRIEF DESCRIPTION OF THE FIGURES

Certain examples are described below with reference to the accompanying figures in which:

FIG. 26A shows ionic gold uptake and FIG. 26B shows nanoparticle gold uptake by cells;

FIGS. 31A, 31B, 31C and 31D show cisplatin time course results for a cell line;

FIGS. 32A, 32B, 32C and 32D show cisplatin time course results for another cell line;

FIGS. 34A and 34B show the results of the serum starvation experiments where the mean intensity was determined for each time point and plotted.

It will be recognized by the person of ordinary skill in the art, given the benefit of this disclosure, that the exemplary spray chambers and other devices shown in the figures may not be to scale. Certain features or dimensions of the spray chambers may have been enlarged, reduced or distorted relative to other features to facilitate a better understanding of aspects and examples disclosed herein. The particular angle at which the sample is introduced into a torch is not from the spray chamber is not intended to be limited by those shown in the figures. Instead, the fluid flows described in reference to the figures are shown merely for illustration and to facilitate a better understanding of the technology disclosed herein.

DETAILED DESCRIPTION

Certain examples described below are directed to devices, methods and systems that can be used, for example, to introduce a sample into an ionization device or ionization source. In some configurations, spray chamber configured to provide tangential flow in combination with laminar flow can be used to provide one or more particles or single molecules to an ionization source. In some embodiments, the spray chamber may provide desirable attributes including, but not limited to, wide particle size selection, e.g., 1 nanometer to 100 microns, reduced internal droplet deposition and/or the ability to provide a single particle or single molecule to the ionization source.

Figure 1:
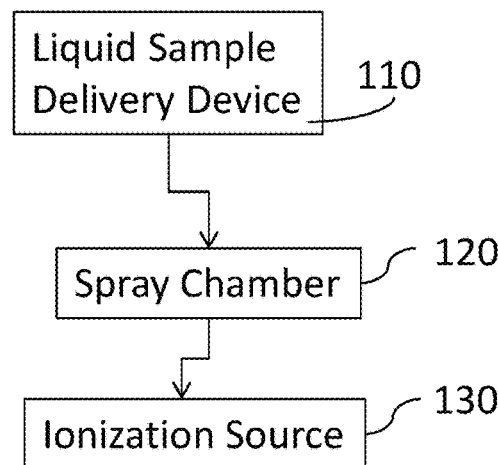
FIG. 1 is a block diagram showing certain components which can be used with a spray chamber, in accordance with certain examples.

In some examples, a spray chamber is generally one component of a sample introduction device or system designed to receive and aerosolize a liquid sample for introduction into a downstream ionization source. A simplified block diagram is shown in FIG. 1. A liquid sample delivery device, e.g., a nebulizer or injector, 110 is fluidically coupled to a spray chamber 120 such that sample from the device 110 can be provided to the spray chamber 120. The device 110 may also be physically coupled to the spray chamber 120 at an inlet of the spray chamber. The spray chamber 120 is fluidically coupled to the ionization source 130 such that aerosolized sample can be sprayed into the ionization source 130. The exact rate at which sample is provided into the device 110 may vary, e.g., from about 1 microliter/minute to about 1 mL/minute, and sample is typically provided into the device 110 by way of a pump fluidically coupled to the device 110. In some instances, flow rates as low as 100 nanoliters/minute up to about 30 microliters/minute can be used or flow rates of about 2 microliters/minute up to about 50 microliters/minute can be used. Liquid sample is typically provided at a constant rate to the device 110, though the flow rate can be altered as desired. One or more gases can be introduced into the spray chamber 120 to break up the liquid into aerosolized droplets. Without wishing to be bound by any particular theory, the ionization source 130 is typically inefficient at desolvating large droplets. Further, the introduction of large droplets into the ionization source 130 can result in rapid temperature drops, e.g., can create hot and cold zones, and can even extinguish the ionization source. The spray chamber 120 can be configured to introduce droplets of a smaller size into the ionization source 130. In some configurations, larger droplets are collected at a drain of the spray chamber and exit the spray chamber. A tangential flow of gas through the spray chamber 120 is effective to select out particles according to their size. Smaller droplets can pass through the spray chamber 120 and onto the ionization source 130 as they are carried in a gas stream which exits the spray chamber 120. In some embodiments, the use of various gas flows in the spray chambers described herein can provide a wider range of particle sizes, e.g., ranging from 1 nanometer in diameter to 100 microns in diameter on average. For example, the spray chambers described herein can be used in single particle inductively coupled mass spectrometry or in other analytical techniques where it may be desirable to analyze single molecules or single particles or single biological cells.

In certain embodiments, the spray chambers described herein may comprise one or more features to enhance delivery of a sample to an ionization source. For example, in some instances, the spray chamber may be configured to provide laminar flow, at least in certain areas, to reduce deposition of droplets in one or more portions of the spray chamber. In other configurations, the spray chamber may comprise microchannels positioned around an inner tube of the spray chamber to reduce or prevent droplets from being deposited on the inner tube. In other instances, the spray chamber may be configured with a dual make up gas inlet to provide enhanced tangential flow within the spray chamber. Combinations of these structural components may also be present in the spray chamber to enhance sample delivery, e.g., the spray chamber may comprise each of a dual make up gas inlet, microchannels positioned around an inner tube and be configured to provide a laminar flow. Various illustrative configurations of spray chambers are described in more detail below.

Figure 2:
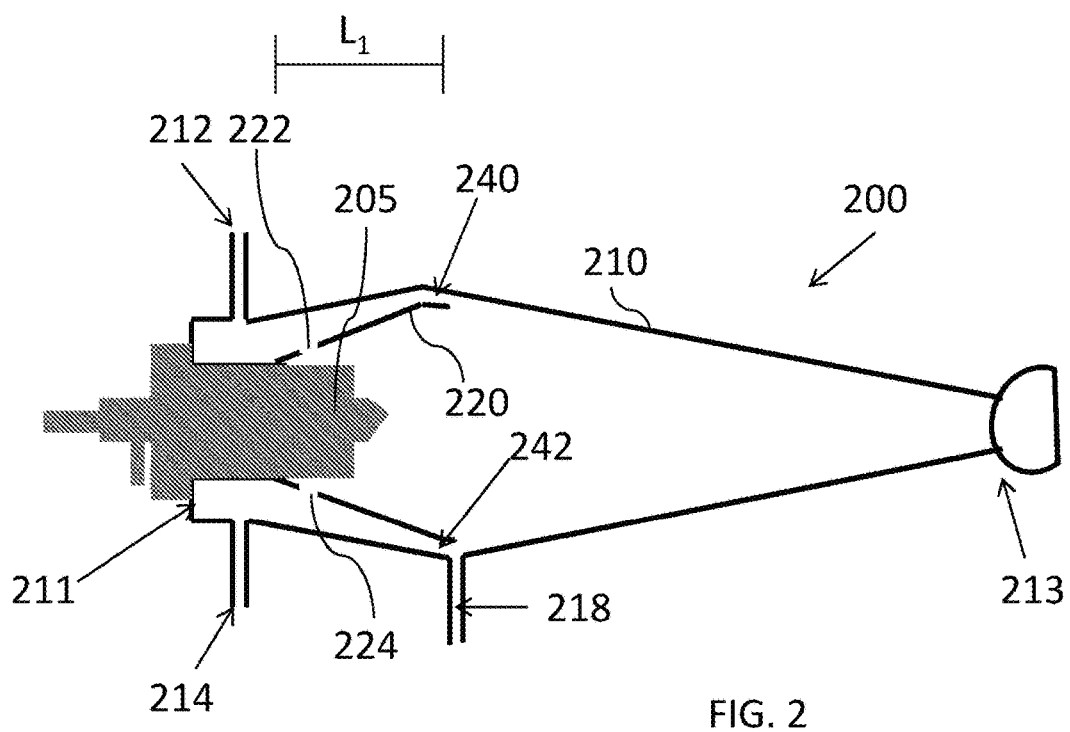
FIG. 2 is one illustration of a spray chamber, in accordance with certain examples.

In certain configurations and referring to FIG. 2, one configuration of a spray chamber 200 is shown. The spray chamber 200 generally comprises an outer chamber or tube 210 and an inner tube 220. The outer chamber 210 comprises dual makeup gas inlets 212, 214 and a drain 218. The makeup gas inlets 212, 214 are typically fluidically coupled to a common gas source, though different gases could be used if desired. While not required, the makeup gas inlets 212, 214 are shown as being positioned adjacent to an inlet end 211, though as noted below they could instead be positioned centrally or toward an outlet end 213. The inner tube 220 is positioned adjacent to a nebulizer tip 205 and comprises two or more microchannels 222, 224 configured to provide a makeup gas flow to reduce or prevent droplets from back flowing and/or depositing on the inner tube 220. The configuration and positioning of the inner tube 220 provides laminar flow at areas 240, 242 which acts to shield inner surfaces of the outer chamber 210 from any droplet deposition. The tangential gas flow provided by way of gas introduction into the spray chamber 200 through the inlets 212, 214 acts to select particles of a certain size range. The microchannels 222, 224 in the inner tube 220 also are designed to permit the gas flows from the makeup gas inlets 212, 214 to shield the surfaces of the inner tube 220 from droplet deposition. In certain examples, the microchannels 222, 224 can be configured in a similar manner, e.g., have the same size and/or diameter, whereas in other configurations the microchannels 222, 224 may be sized or arranged differently. In some instances, at least two, three, four, five or more separate microchannels can be present in the inner tube 220. The exact size, form and shape of the microchannels may vary and each microchannel need not have the same size, form or shape. In some examples, different diameter microchannels may exist at different radial planes along a longitudinal axis $L_1$ of the inner tube to provide a desired shielding effect.

In certain embodiments, the exact dimensions of the spray chamber may vary. In certain configurations, a longitudinal length from the nebulizer tip 205 to the end of the spray chamber 200 may be about 10 cm to about 15 cm, e.g., about 12 or 13 cm. The diameter of the outer tube 210 may vary from about 1 cm to about 5 cm, e.g., about 3 cm or 4 cm. The largest diameter of the inner tube 220 may vary from about 0.5 cm to about 4 cm, and the distance between outer surfaces of the inner tube 220 and inner surfaces of the outer tube 210 can be selected to provide a desired laminar flow rate, e.g., the distance may be about 0.1 cm to about 0.75 cm.

Figure 3:
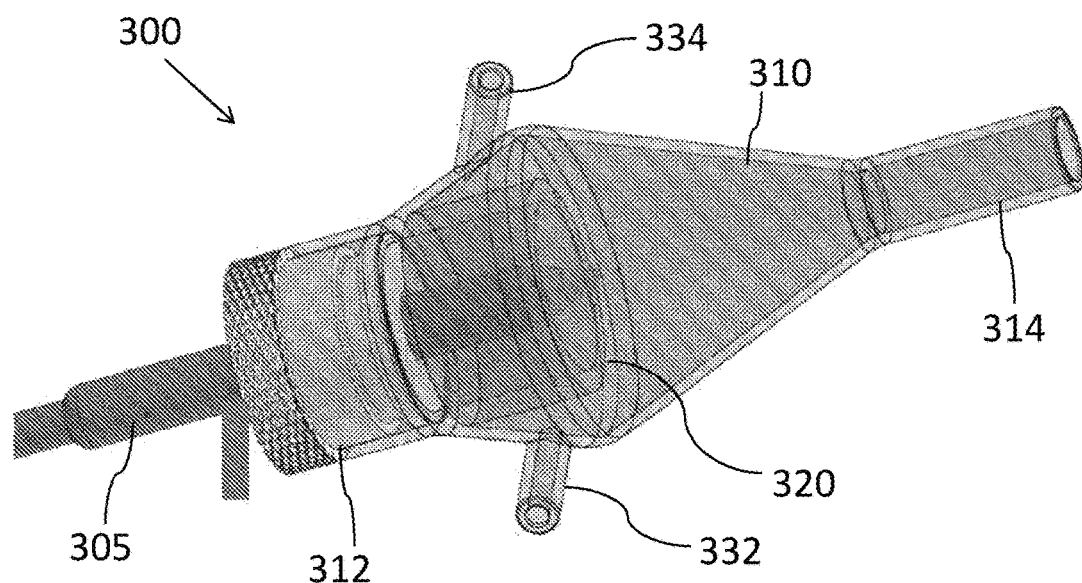
FIG. 3 is another illustration of a spray chamber, in accordance with certain configurations.
Figure 4:
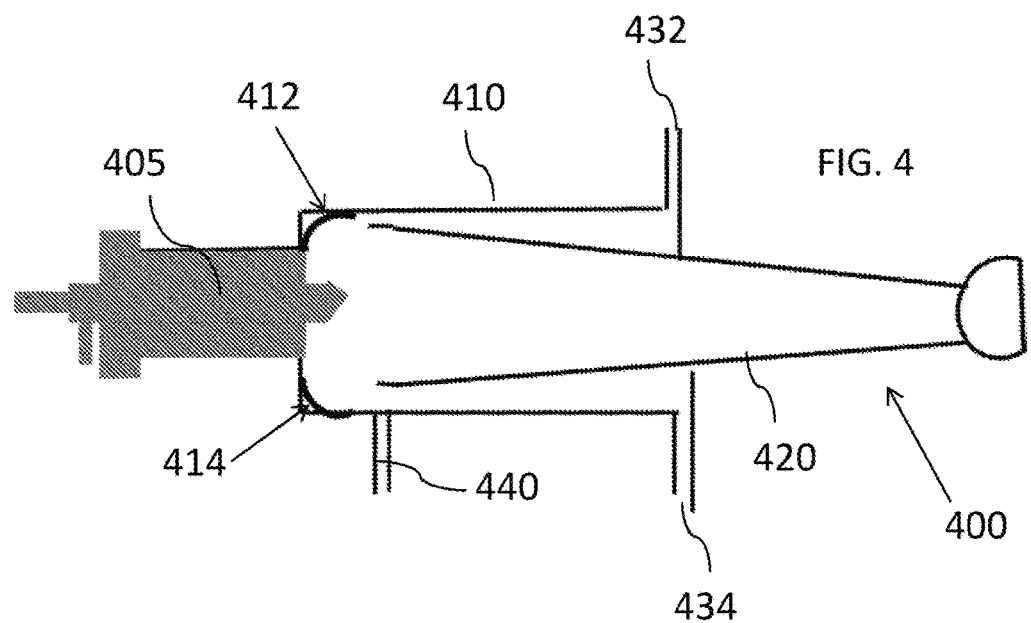
FIG. 4 is an additional configuration of a spray chamber, in accordance with certain examples.
Figure 5A:
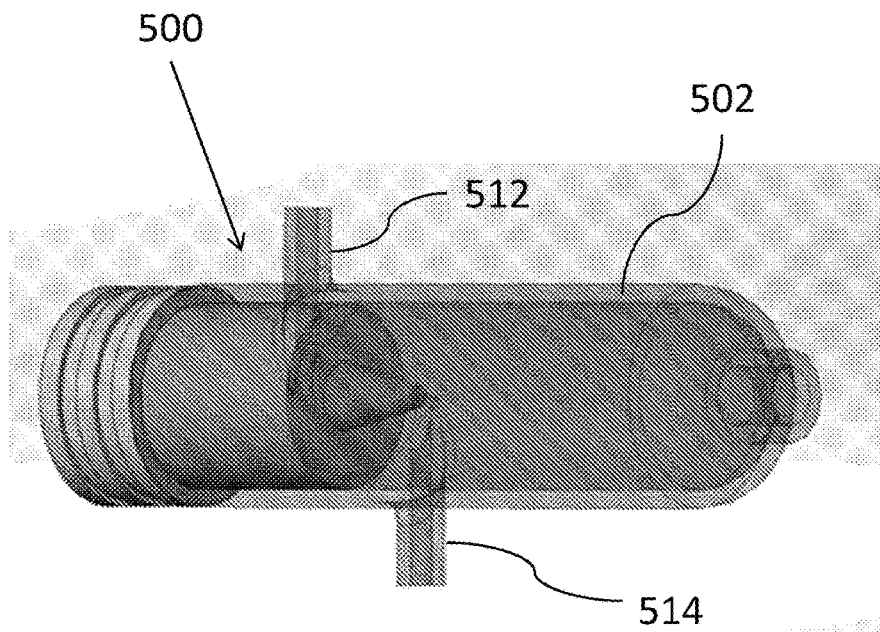
FIGS. 5A, 5B, 5C, 5D and 5E are illustrations of another spray chamber, in accordance with certain embodiments.
Figure 5B:
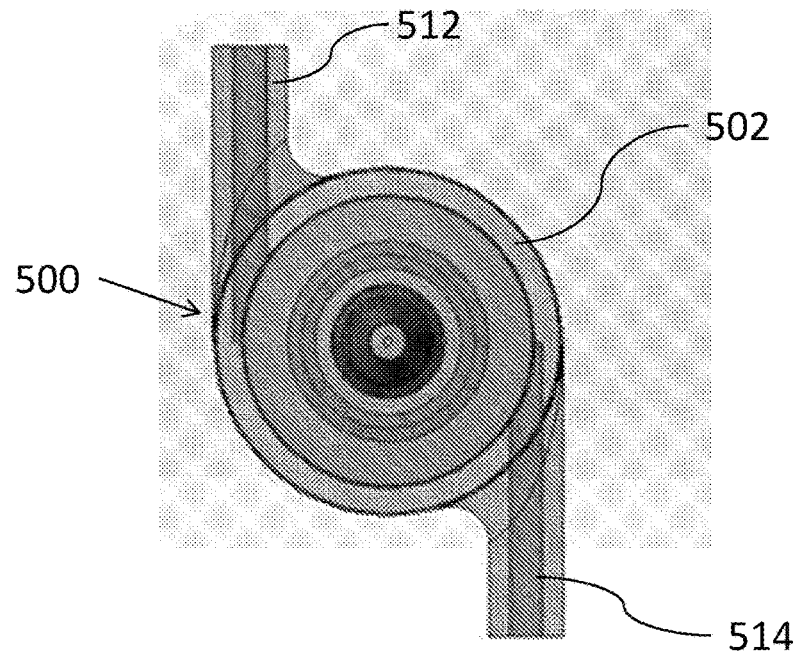
Figure 5C:
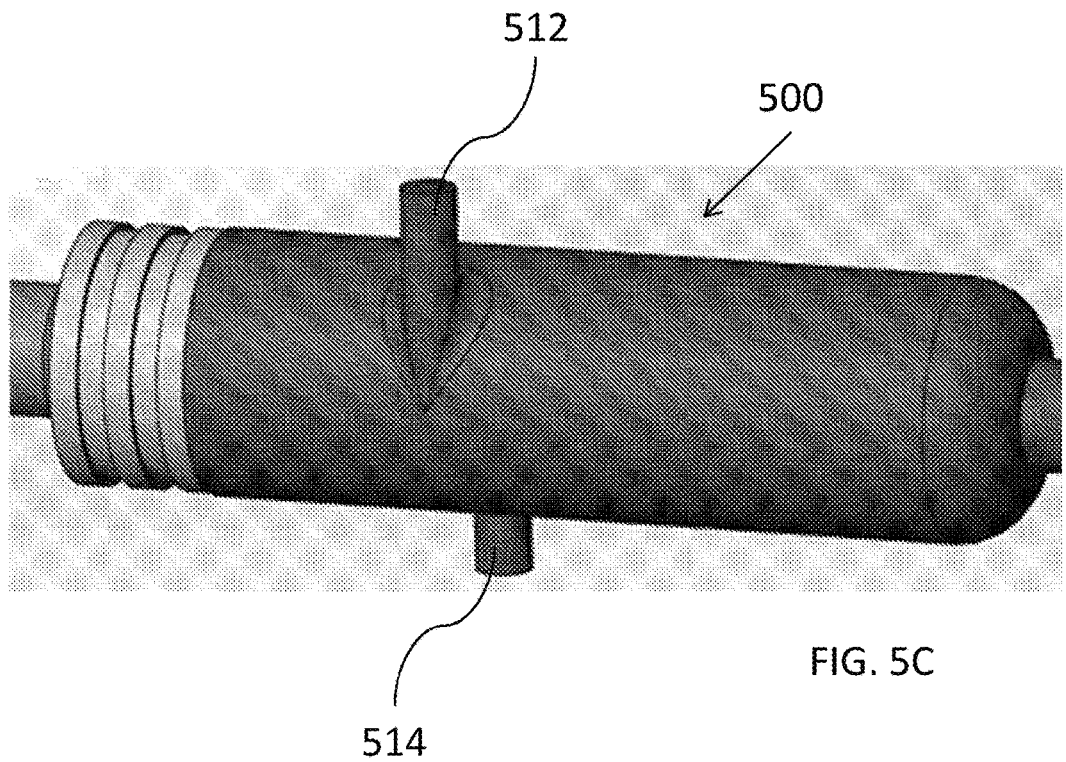
Figure 5D:
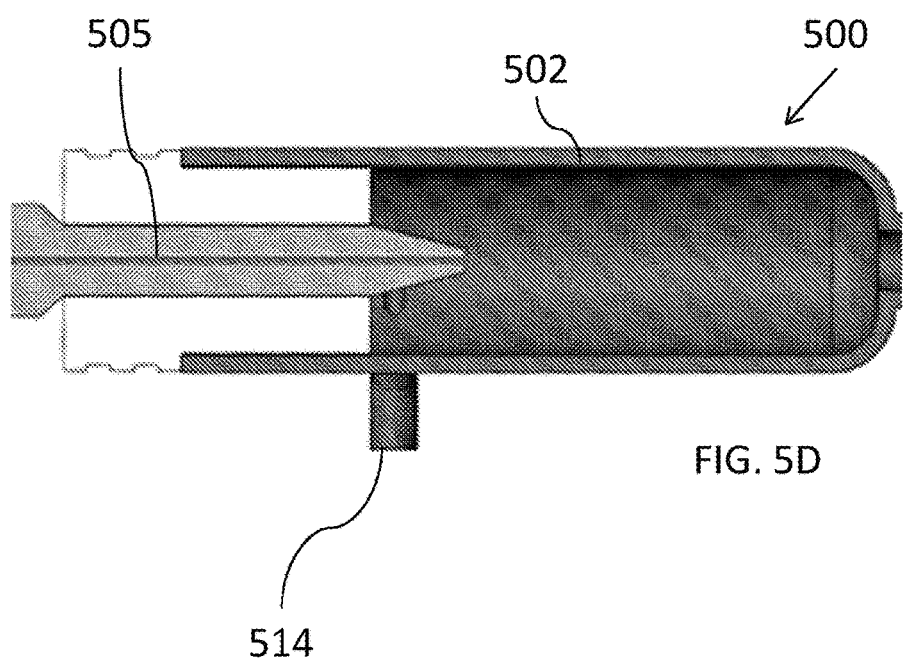
Figure 5E:
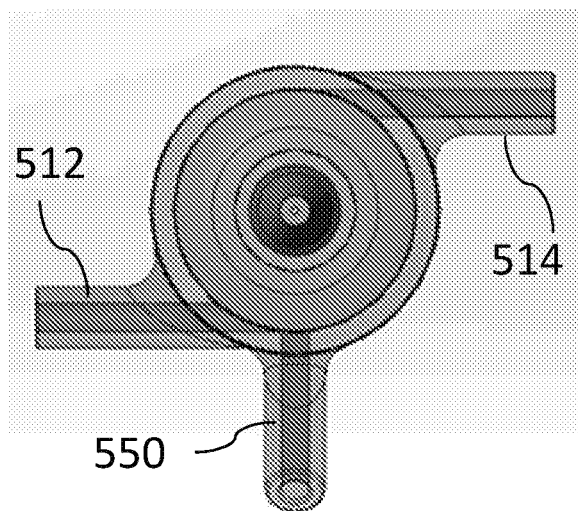

In certain examples, the inner tube 220 is shown as having a generally increasing internal diameter along the longitudinal axis of the outer chamber 210, though as noted herein this dimensional change is not required. Some portion of the inner tube 220 may be "flat" or generally parallel with the longitudinal axis $L_1$ to enhance the laminar flow, or in an alternative configuration, some portion of the inner tube 220 may generally be parallel to the surface of the outer tube 210, at least for some length, to enhance laminar flow. The inner diameter of the outer chamber increases from the inlet end 211 toward the outlet end 213 up to a point and then decreases toward the outlet end 213 such that the inner diameter of the outer chamber 210 is smaller at the outlet end 213 than at the inlet end 211. As noted in more detail below, however, the inner diameter of the outer chamber 210 may remain constant from the inlet end toward the outlet end or may increase from the inlet end toward the outlet end.

In certain configurations and referring to FIG. 3, another illustration of a spray chamber is shown. The spray chamber 300 comprises an outer chamber 310 and an inner tube 320. An inner diameter of the inner tube 320 is substantially constant along a direction from an inlet end 312 of the outer chamber 310 to an outlet end 314 of the outer chamber 310. The inner tube outer diameter generally increases from the inlet end 312 to the outlet end 314, e.g., the overall outer shape of the inner tube 320 is a cone. The inner tube 320 may optionally comprise one or more internal microchannels (not shown) to assist in preventing droplet formation on the inner tube and/or sample backflow when sample is introduced into the spray chamber 300 from a nebulizer 305. The outer chamber 310 also comprises dual makeup gas inlets 332, 334 which can be fluidically coupled to the same or different gas sources. Gas can be introduced into the spray chamber 300 through the makeup gas inlets 332, 334 to provide a tangential flow to aerosolize and select particles of a certain size from the particles introduced from the nebulizer 305. Gas from the inlets 332, 334 can also pass through any microchannels in the inner tube 320 to reduce the likelihood of droplet formation on the inner tube surfaces. A laminar flow may also be provided by positioning the inner tube 320 in a suitable manner relative to the outer chamber 310. For example, the outer chamber 310 at its widest point may be about 0.1-0.75 cm from an outer surface of the inner tube 320 to provide a laminar flow that can shield the outer chamber 310 from droplet formation. While not shown, a drain port may also be present in the outer chamber 310 to permit very large droplets, e.g., those having a size in excess of 100 microns, to drain out of the chamber 310.

In another embodiment and referring to FIG. 4, another configuration of a spray chamber is shown. The spray chamber 400 comprises an outer chamber 410 and an inner tube 420. The outer chamber 410 comprises rounded edges 412, 414 adjacent to an inlet of the outer chamber 410. While not wishing to be bound by any particular theory, the rounded edges can assist in steering laminar flows in the outer chamber 410 and prevent droplet buildup on surfaces of the outer chamber 410. The inner tube 420 tapers from an inlet to an outlet. The outer tube 410 comprises makeup gas inlets 432, 434 to provide for tangential flows within the spray chamber 400. A makeup flow exit port 440 is present to assist in providing laminar flows within the spray chamber 400. The outer chamber 410 generally comprises a constant diameter from an inlet end to an outlet end. While not shown, the inner tube 420 may comprise one or more internal microchannels to reduce the likelihood of droplet formation on surfaces of the inner tube 420.

Another configuration of a spray chamber is shown in FIGS. 5A-5E. Referring to FIG. 5A, a spray chamber comprises an outer chamber 502. A first makeup gas inlet 512 is shown positioned in a different longitudinal plane than a second makeup gas inlet (see FIG. 5B). This configuration can assist in the production of the tangential gas flows. While the inlets 512, 514 are shown as being generally orthogonal to a longitudinal axis of the outer chamber 502, they could instead be angled if desired. The configuration shown in FIGS. 5A-5D may be desirable for use in low volume applications, e.g., where small amounts of fluid less than 50 microliters or less than 30 microliters are used to select single particles or single cells including, for example, Single Particle-ICP-MS (SP-ICP-MS), Single Cell-ICP-MS (SC-ICP-MS, and Capillary Electrophoresis-ICP-MS (CE-ICP-MS). The overall volume of the spray chamber shown in FIGS. 5A-5D may be, for example, about 6-12 $cm^3$, e.g., about 7-11 $cm^3$ or about 8-10 $cm^3$. For comparison purposes, the volume of the spray chambers shown in FIGS. 2-4 may be, for example, 30 $cm^3$ up to about 50 $cm^3$. The makeup gas inlets 512, 514 and overall shape and dimensions of the spray chamber 500 helps in maximizing the transport efficiency of aerosols to the plasma. Dimensions are chosen in a way that the axial nebulizer flow (or flow from a different liquid sample delivery device) misses the walls so that the majority of aerosols will be carried straight to the plasma. The dual gas inlet design for the introduction of make-up gas can provide or promote formation of a swirl flow field that can assist in containing the aerosols that are diffusing out of the main nebulizer stream due to turbulence and the eddies and keeping them away from the walls, e.g., droplet formation/wall condensation can be reduced. As noted in more detail in the examples appended below, simulation results for droplet transport show that a transport efficiency of greater than 90% can be achieved with the spray chambers described herein. As noted herein, the outer chamber 502 may comprise rounded edges at the inlet end to promote the laminar flow. In other configurations, the outer chamber 502 may comprise a drain port (see drain port 550 in FIG. 5E). In some examples, the dual gas inlets 512, 514 are positioned adjacent to the inlet end of the outer chamber 502. In other examples, the dual gas inlets 512, 514 are positioned adjacent to the outlet end of the outer chamber 502. As shown in FIGS. 5A-5D, an outer diameter of the outer chamber 502 is substantially constant in a longitudinal direction. In some instances, an inner tube (not shown) can be positioned within the outer chamber 502, wherein the inner tube comprises a plurality of microchannels each configured to receive the makeup gas to prevent droplets of the liquid sample from depositing on surfaces of the inner tube. The inner tube can be positioned to provide a laminar flow within the outer chamber 502 to prevent droplet formation on inner surfaces of the outer chamber.

In certain embodiments, the spray chambers described herein can be used in tandem with one or more additional spray chambers. Referring to FIG. 6A, a block diagram showing a first spray chamber 610 fluidically coupled to a second spray chamber 620 is shown. Each of the spray chambers 610, 620 may be one of the spray chambers described herein or one of the spray chambers 610, 620 may be one of the spray chambers described herein and the other spray chamber may be a conventional double pass spray chamber or a conventional cyclonic spray chamber. While not wishing to be bound by any particular illustration, in a double pass spray chamber smaller aerosol droplets are directed into a central tube and the larger aerosol droplets are removed by gravity and exit the chamber through a drain. The smaller droplets can be provided to a downstream ionization source. In a cyclonic spray chamber, a vortex produced by tangential gas flows can be used to provide a centrifugal force to the droplets. Smaller droplets are provided in the exiting gas stream, while the larger droplets contact the inner walls of the chamber and are removed through a drain. In some examples, the spray chamber 610 may be a double pass spray chamber and the spray chamber 620 may be one of the spray chambers described herein. In other examples, the spray chamber 610 may be one of the spray chambers described herein and the spray chamber 620 may be a double pass spray chamber. In additional configurations, the spray chamber 610 may be a cyclonic spray chamber and the spray chamber 620 may be one of the spray chambers described herein. In other examples, the spray chamber 610 may be one of the spray chambers described herein and the spray chamber 620 may be a cyclonic spray chamber. In some configurations, each of the spray chambers 610, 620 may be one of the spray chambers described herein, but the dimensions of the microchannels present in an inner tube may be different. In other configurations, one of the spray chambers 610, 620 may be the spray chamber shown in FIG. 2 and the other spray chamber may be one of the spray chamber shown in FIGS. 3-5D. In certain configurations, one of the spray chambers 610, 620 may be the spray chamber shown in FIG. 3 and the other spray chamber may be the spray chamber shown in FIG. 2, 4 or 5A-5D. In some examples, one of the spray chambers 610, 620 may be the spray chamber shown in FIG. 4 and the other spray chamber may be the spray chamber shown in FIG. 2, 3 or 5A-5D. While not shown, three or more spray chambers can be fluidically coupled to each other if desired.

In certain examples, illustrative liquid sample delivery devices suitable for use with the spray chambers described herein include, but are not limited to, nebulizer, injectors, capillary tubing etc. In some embodiment, a nebulizer physically couples to the spray chamber to introduce liquid sample into the spray chamber. The nebulizer can take many forms including crossflow nebulizers, concentric nebulizers and microflow nebulizers. Where injectors are used, the injector may take the form of a needle, capillary or other tubing with a small orifice. Additional liquid sample delivery devices for use with the spray chambers described herein will be selected by the person of ordinary skill in the art, given the benefit of this disclosure. For example, ultrasonic pulse liquid delivery devices, droplet generators or microdrop generators can also be used with the spray chambers described herein. In addition, the nebulizer (or other liquid delivery device) can be hyphenated to one or more upstream devices or instruments, e.g., liquid chromatography devices, capillary electrophoresis devices, cell sorters, cell handling apparatus, and the like.

Figure 6A:
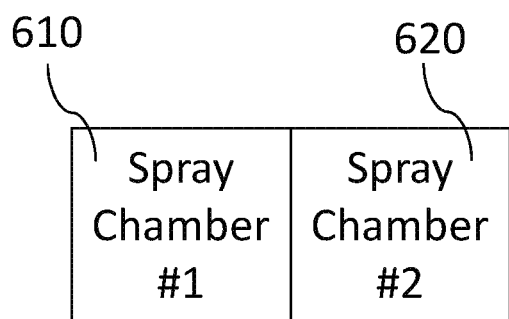
FIG. 6A is a block diagram showing two spray chambers fluidically coupled to each other, in accordance with certain examples.
Figure 6B:
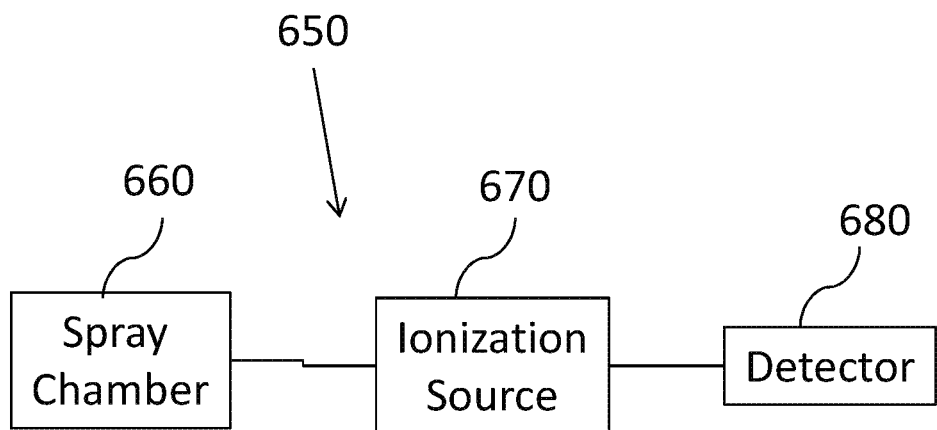
FIG. 6B is a block diagram showing a spray chamber used with an ionization source and a detector, in accordance with certain embodiments.

In certain examples, the spray chambers described herein can be used in combination with one or more ionization sources and/or detectors. A simplified block diagram is shown in FIG. 6B. The system 650 comprises a spray chamber 660 fluidically coupled to an ionization source 670. The ionization source 670 can be fluidically coupled, optically coupled, etc. to a detector 680 for detection of species which are ionized/atomized by the ionization source 670. The exact nature of the ionization source 670 can vary, and illustrative types of ionization sources 670 include, but are not limited to, inductively coupled plasmas, capacitively coupled plasmas, microwave-induced plasmas, low flow plasmas, arcs, sparks, flames and other high temperature or high energy sources which can ionize and/or atomize a sample, e.g., a sample comprising an inorganic material or an organic material. In some examples, the ionization source 670 may be configured as a source which can implement one or more techniques including but not limited to, electron ionization, chemical ionization, desorption chemical ionization, negative-ion chemical ionization, field desorption, field ionization, fast atom bombardment, secondary ion mass spectrometry, electrospray ionization, probe electrospray ionization, sonic spray ionization, atmospheric pressure chemical ionization, atmospheric pressure photoionization, atmospheric pressure laser ionization, matrix assisted laser desorption ionization, aerosol laser desorption ionization, surface-enhanced laser desorption ionization, glow discharges, resonant ionization, thermal ionization, thermospray ionization, radioactive ionization, ion-attachment ionization, liquid metal ion devices, laser ablation electrospray ionization, or combinations of any two or more of these illustrative ionization techniques. The detector 680 may take numerous forms depending on the sample species to be detected, and illustrative detectors include optical detectors, particle detectors, electron detectors and ion detectors.

Figure 7:
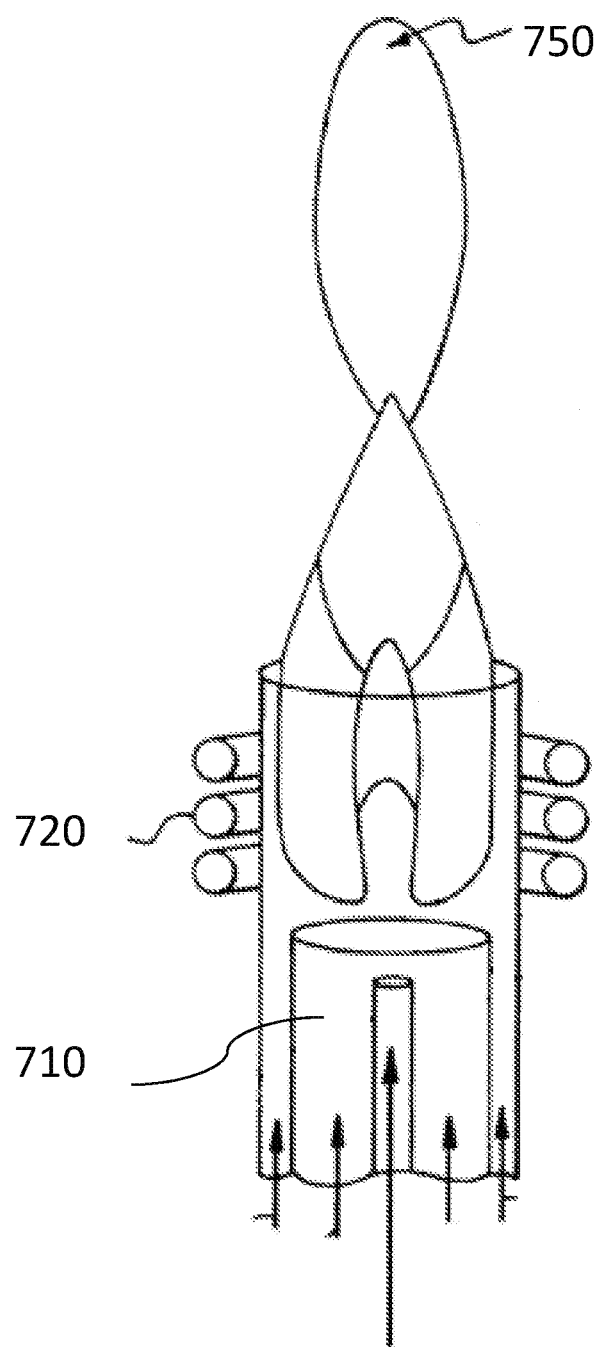
FIG. 7 is an illustration of an ionization device comprising a torch and an induction coil, in accordance with certain examples.
Figure 8:
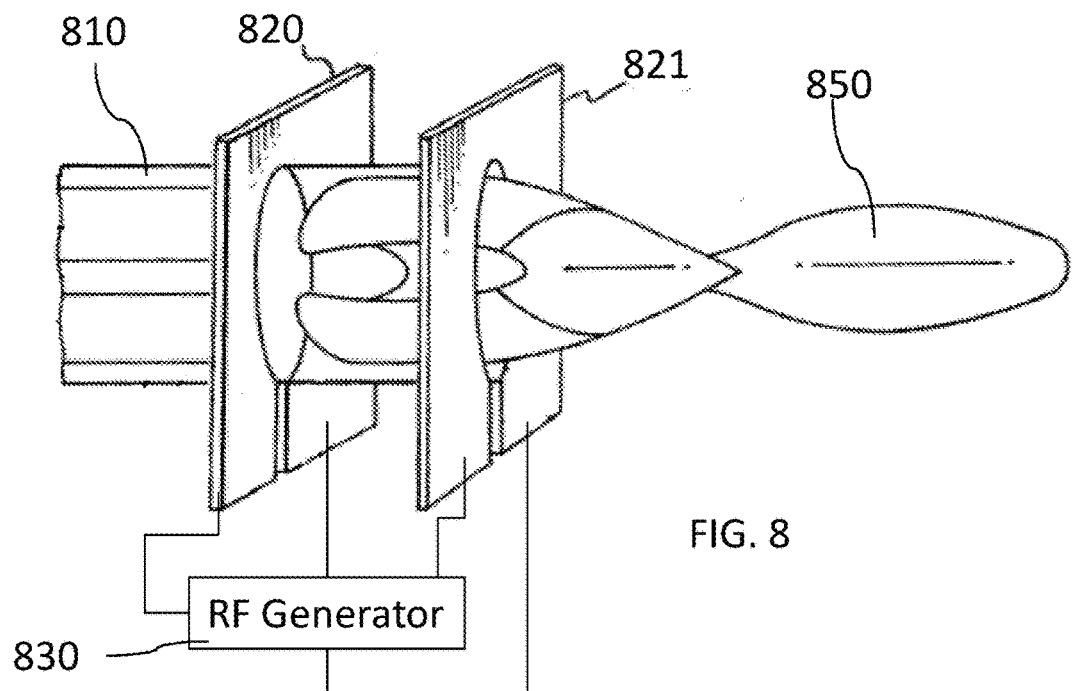
FIG. 8 is an illustration of an ionization device comprising a torch and two plate electrodes, in accordance with certain configurations.
Figure 9:
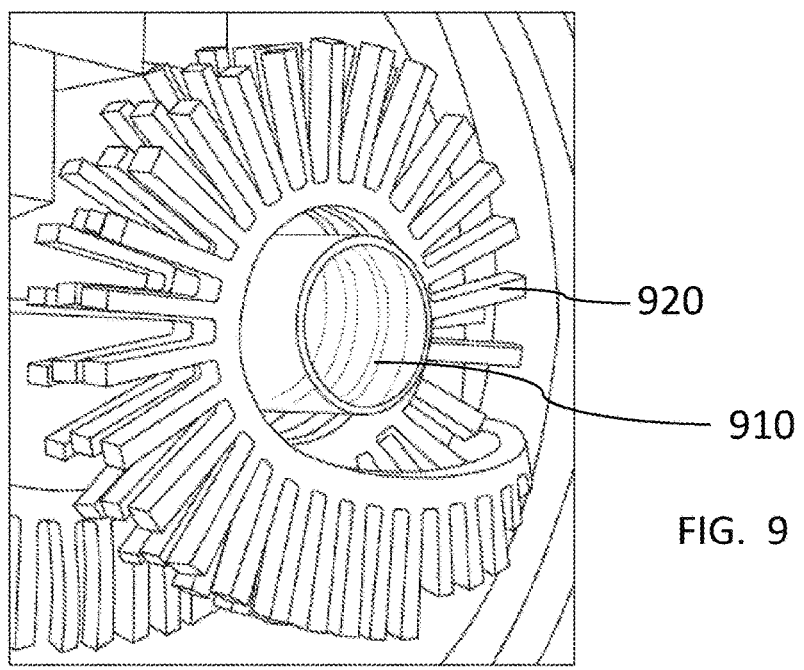
FIG. 9 is an illustration of an induction coil comprising radial fins, in accordance with certain examples.

In certain examples, the ionization source may comprise one or more torches and one or more induction devices. Certain components of an ionization source are shown in FIGS. 7-9. Illustrative induction devices and torches are described, for example, in U.S. Pat. Nos. 9,433,073 and 9,360,403, the entire disclosure of which is hereby incorporated herein by reference for all purposes. Referring to FIG. 7, a device comprising a torch 710 in combination with an induction coil 720 is shown. The induction coil 720 is typically electrically coupled to a radio frequency generator (not shown) to provide radio frequency energy into the torch 710 and sustain an inductively coupled plasma 750. A spray chamber as described herein can be used to spray sample into the plasma 750 to ionize and/or atomize species in the sample. If desired, the spray chamber can be configured similar to those shown in FIGS. 2-4 or may comprise tandem or double spray chambers as described herein. In a typical configuration, a nebulizer is fluidically coupled to a spray chamber to provide liquid sample to the spray chamber. The spray chamber aerosolizes the sample and provides it to the plasma 750. Metal species (or organic species) in the sample can be ionized or atomized and detected using optical techniques or mass spectrometry techniques or other suitable techniques.

In an alternative configuration, the induction coil 720 could be replaced with one or more plate electrodes. For example and referring to FIG. 8, a first plate electrode 820 and a second plate electrode 821 are shown as comprising an aperture that can receive a torch 810. For example, the torch 810 can be placed within some region of an induction device comprising plate electrodes 820, 821. A plasma or other ionization/atomization source 850 such as, for example, an inductively coupled plasma can be sustained using the torch 810 and inductive energy from the plates 820, 821. A radio frequency generator 830 is shown as electrically coupled to each of the plates 820, 821. If desired, only a single plate electrode could be used instead. A spray chamber as described herein can be used to spray sample into the plasma 850 to ionize and/or atomize species in the sample. If desired, the spray chamber used with the component of FIG. 8 can be configured similar to those shown in FIGS. 2-4 or may comprise tandem or double spray chambers as described herein. In a typical configuration, a nebulizer is fluidically coupled to a spray chamber to provide liquid sample to the spray chamber. The spray chamber aerosolizes the sample and provides it to the plasma 850. Metal species (or organic species) in the sample can be ionized or atomized and detected using optical techniques or mass spectrometry techniques or other suitable techniques.

In other configurations, an induction device comprising one or more radial fins could instead be used in combination with the spray chambers described herein. Referring to FIG. 9, a device or system may comprise an induction coil 920 comprising at least one radial fin and a torch 910. A plasma or other ionization/atomization source (not shown) such as, for example, an inductively coupled plasma can be sustained using the torch 910 and inductive energy from the radially finned induction device 920. A radio frequency generator (not shown) can be electrically coupled to the induction device 920 to provide radio frequency energy into the torch 910. The spray chamber used with the components of FIG. 9 can be configured similar to those shown in FIGS. 2-4 or may comprise tandem or double spray chambers as described herein. In a typical configuration, a nebulizer is fluidically coupled to a spray chamber to provide liquid sample to the spray chamber. The spray chamber aerosolizes the sample and provides it to the plasma. Metal species (or organic species) in the sample can be ionized or atomized and detected using optical techniques or mass spectrometry techniques or other suitable techniques.

In other instances, one or more capacitive device such as, for example, capacitive coils or capacitive plates can be used in combination with the spray chambers described herein. Further two or more induction devices, capacitive devices or other devices which can provide energy into the torch to sustain an atomization/ionization source such as a plasma or flame can also be used in combination with the spray chambers described herein.

Figure 10:
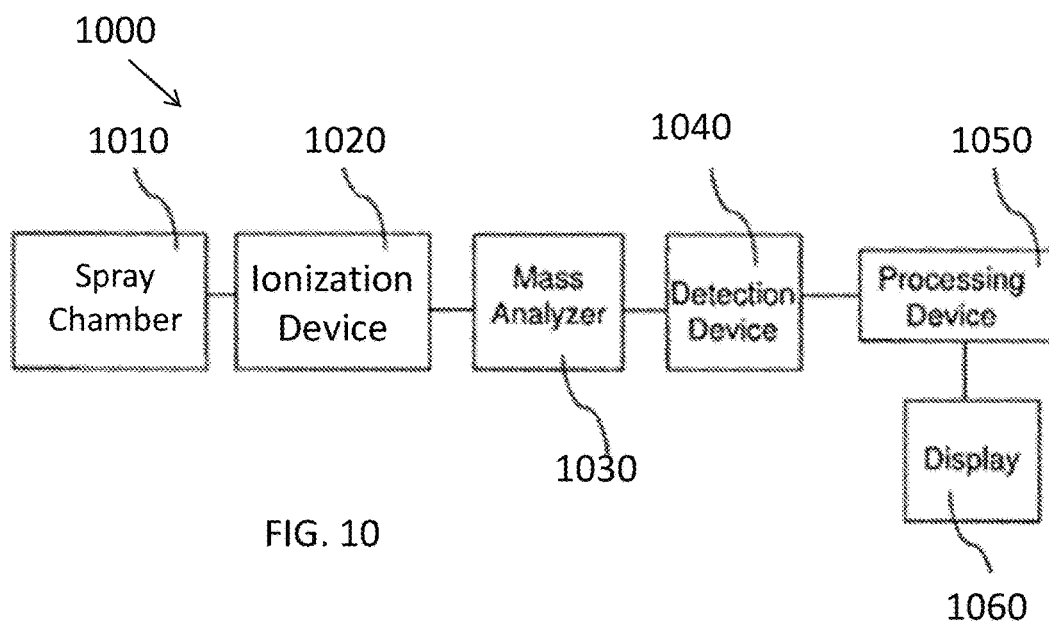
FIG. 10 is a block diagram of a mass spectrometer comprising a spray chamber as described herein, in accordance with certain examples.

In certain configurations, the spray chambers described herein can be used in a system configured to perform mass spectrometry (MS). For example and referring to FIG. 10, a MS device or system 1000 includes a spray chamber 1010, an ionization device, 1020, e.g., a torch and induction device that can be used to sustain an atomization/ionization source such as a plasma, a mass analyzer 1030, a detector or detection device 1040, a processor or processing device 1050 and a display 1060. The spray chamber 1010, ionization device 1020, the mass analyzer 1030 and the detection device 1040 may be operated at reduced pressures using one or more vacuum pumps. In certain examples, however, only the mass analyzer 1030 and the detection device 1040 may be operated at reduced pressures. While not shown the spray chamber 1010 is typically fluidically coupled to a nebulizer, injector or other device to introduce liquid sample into the spray chamber 1010. The ionization device 1020 may comprise one or more components as illustrated in FIGS. 7-9 or other devices and components which can provide or sustain an ionization source. The mass analyzer 1030 may take numerous forms depending generally on the sample nature, desired resolution, etc. and exemplary mass analyzers may comprise one or more rod assemblies such as, for example, a quadrupole or other rod assembly. In some examples, the mass analyzer 1030 may be, or may include, a time of flight device. In some instances, the mass analyzer 1030 may comprise its own radio frequency generator. The detection device 1040 may be any suitable detection device that may be used with existing mass spectrometers, e.g., electron multipliers, Faraday cups, coated photographic plates, scintillation detectors, multi-channel plates, etc., and other suitable devices that will be selected by the person of ordinary skill in the art, given the benefit of this disclosure. The processing device 1050 typically includes a microprocessor and/or computer and suitable software for analysis of samples introduced into the MS device 1000. One or more databases may be accessed by the processing device 1050 for determination of the chemical identity of species introduced into the MS device 1000. Other suitable additional devices known in the art may also be used with the MS device 1000 including, but not limited to, autosamplers, such as AS-90plus and AS-93plus autosamplers commercially available from PerkinElmer Health Sciences, Inc. It will also be within the ability of the person of ordinary skill in the art, given the benefit of this disclosure, to retrofit existing MS devices with the spray chambers described herein and to design new MS devices using the spray chambers described herein.

Figure 11:
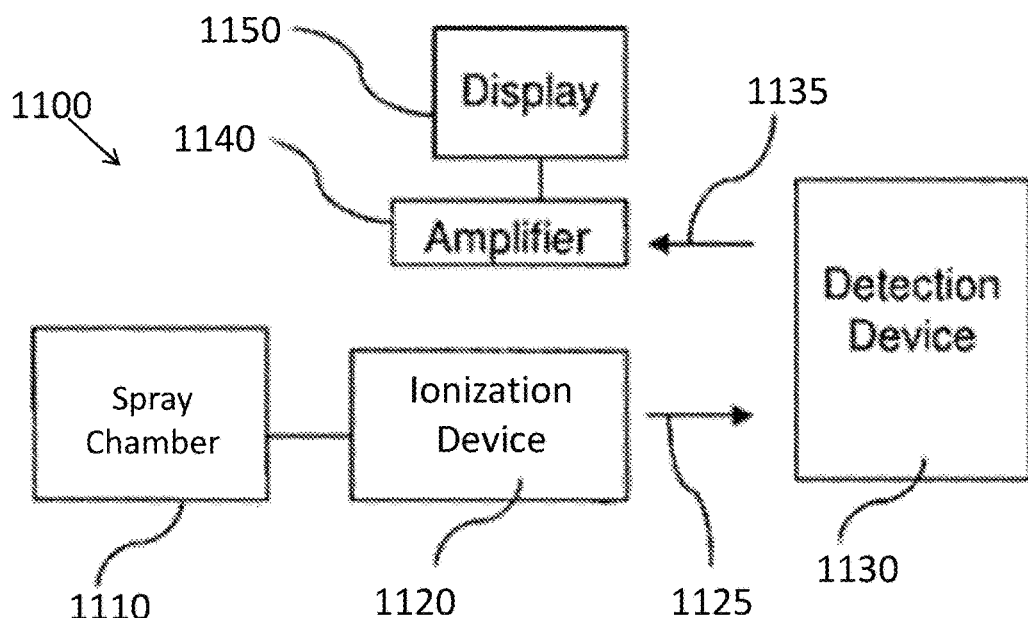
FIG. 11 is a block diagram of an optical emission spectrometer comprising a spray chamber as described herein, in accordance with certain examples.

In certain configurations, the spray chambers described herein can be used in optical emission spectroscopy (OES). Referring to FIG. 11, an OES device or system 1100 includes a spray chamber 1110, an ionization device 1120 and a detection device 1130. The spray chamber 1110 may be fluidically coupled to a nebulizer to aerosolize liquid sample for introduction into the ionization device 1120. The ionization device 1120 may comprise one or more components as illustrated in FIGS. 7-9 or other devices and components which can provide or sustain an ionization source. The detector or detection device 1130 may take numerous forms and may be any suitable device that may detect optical emissions, such as optical emission 1125. For example, the detection device 1130 may include suitable optics, such as lenses, mirrors, prisms, windows, band-pass filters, etc. The detection device 1130 may also include gratings, such as echelle gratings, to provide a multi-channel OES device. Gratings such as echelle gratings may allow for simultaneous detection of multiple emission wavelengths. The gratings may be positioned within a monochromator or other suitable device for selection of one or more particular wavelengths to monitor. In certain examples, the detection device 1130 may include a charge coupled device (CCD). In other examples, the OES device 1100 may be configured to implement Fourier transforms to provide simultaneous detection of multiple emission wavelengths. The detection device 1130 may be configured to monitor emission wavelengths over a large wavelength range including, but not limited to, ultraviolet, visible, near and far infrared, etc. The OES device 1100 may further include suitable electronics such as a microprocessor and/or computer and suitable circuitry to provide a desired signal and/or for data acquisition. Suitable additional devices and circuitry are known in the art and may be found, for example, on commercially available OES devices such as Optima 2100DV series, Optima 5000 DV series OES devices or Optima 8000 or 8300 series OES devices commercially available from PerkinElmer Health Sciences, Inc. The optional amplifier 1140 e.g., a photomultiplier tube, may be operative to increase a signal 1135, e.g., amplify the signal from detected photons, and provides the signal to display 1150, which may be a readout, computer, etc. In examples where the signal 1135 is sufficiently large for display or detection, the amplifier 1140 may be omitted. In certain examples, the amplifier 1140 is a photomultiplier tube (PMT) configured to receive signals from the detection device 1130. Other suitable devices for amplifying signals, however, will be selected by the person of ordinary skill in the art, given the benefit of this disclosure. If desired the PMT can be integrated into the detector 1130. It will also be within the ability of the person of ordinary skill in the art, given the benefit of this disclosure, to retrofit existing OES devices with the spray chambers disclosed herein and to design new OES devices using the spray chambers disclosed here. The OES devices may further include autosamplers, such as AS90 and AS93 autosamplers commercially available from PerkinElmer Health Sciences, Inc. or similar devices available from other suppliers.

Figure 12:
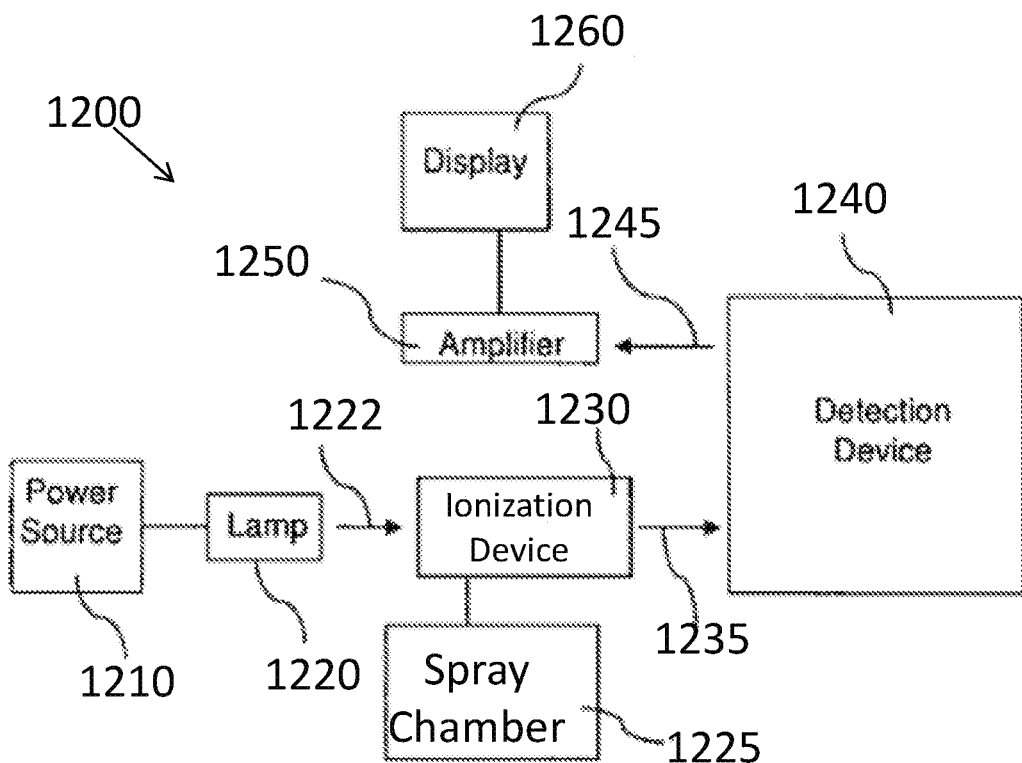
FIG. 12 is a block diagram of an atomic absorption spectrometer comprising a spray chamber as described herein, in accordance with certain examples.

In certain examples, the spray chambers described herein can be used in an atomic absorption spectrometer (AAS). Referring to FIG. 12, a single beam AAS 1200 comprises a power source 1210, a lamp 1220, a spray chamber 1225, an ionization device 1230, a detector or detection device 1240, an optional amplifier 1250 and a display 1260. The power source 1210 may be configured to supply power to the lamp 1220, which provides one or more wavelengths of light 1222 for absorption by atoms and ions. Suitable lamps include, but are not limited to mercury lamps, cathode ray lamps, lasers, etc. The lamp may be pulsed using suitable choppers or pulsed power supplies, or in examples where a laser is implemented, the laser may be pulsed with a selected frequency, e.g. 5, 10, or 20 times/second. The exact configuration of the lamp 1220 may vary. For example, the lamp 1220 may provide light axially along the torch of the ionization device 1230 or may provide light radially along the a torch of the ionization device 1230. The example shown in FIG. 12 is configured for axial supply of light from the lamp 1220. There can be signal-to-noise advantages using axial viewing of signals. The ionization device 1230 may comprise one or more components as illustrated in FIGS. 7-9 or other devices and components which can provide or sustain an ionization source. As sample is atomized and/or ionized in the ionization device 1230, the incident light 1222 from the lamp 1220 may excite atoms. That is, some percentage of the light 1222 that is supplied by the lamp 1220 may be absorbed by the atoms and ions in the ionization device 1230. The remaining percentage of the light 1235 may be transmitted to the detection device 1240. The detection device 1240 may provide one or more suitable wavelengths using, for example, prisms, lenses, gratings and other suitable devices such as those discussed above in reference to the OES devices, for example. The signal may be provided to the optional amplifier 1250 for increasing the signal provided to the display 1260. To account for the amount of absorption by sample in the ionization device 1230, a blank, such as water, may be introduced prior to sample introduction to provide a 100% transmittance reference value. The amount of light transmitted once sample is introduced into the ionization device 1230 may be measured, and the amount of light transmitted with sample may be divided by the reference value to obtain the transmittance. The negative $\log_{10}$ of the transmittance is equal to the absorbance. AAS device 1200 may further include suitable electronics such as a microprocessor and/or computer and suitable circuitry to provide a desired signal and/or for data acquisition. Suitable additional devices and circuitry may be found, for example, on commercially available AAS devices such as AAnalyst series spectrometers or PinAAcle spectrometers commercially available from PerkinElmer Health Sciences, Inc. It will also be within the ability of the person of ordinary skill in the art, given the benefit of this disclosure, to retrofit existing AAS devices with the spray chambers disclosed herein and to design new AAS devices using the spray chambers disclosed herein. The AAS devices may further include autosamplers known in the art, such as AS-90A, AS-90plus and AS-93plus autosamplers commercially available from PerkinElmer Health Sciences, Inc. Where the ionization device 1230 is configured to sustain an inductively coupled plasma, a radio frequency generator electrically coupled to an induction device may be present. In certain embodiments, a double beam AAS device, instead of a single beam AAS device could instead be used.

Figure 13:
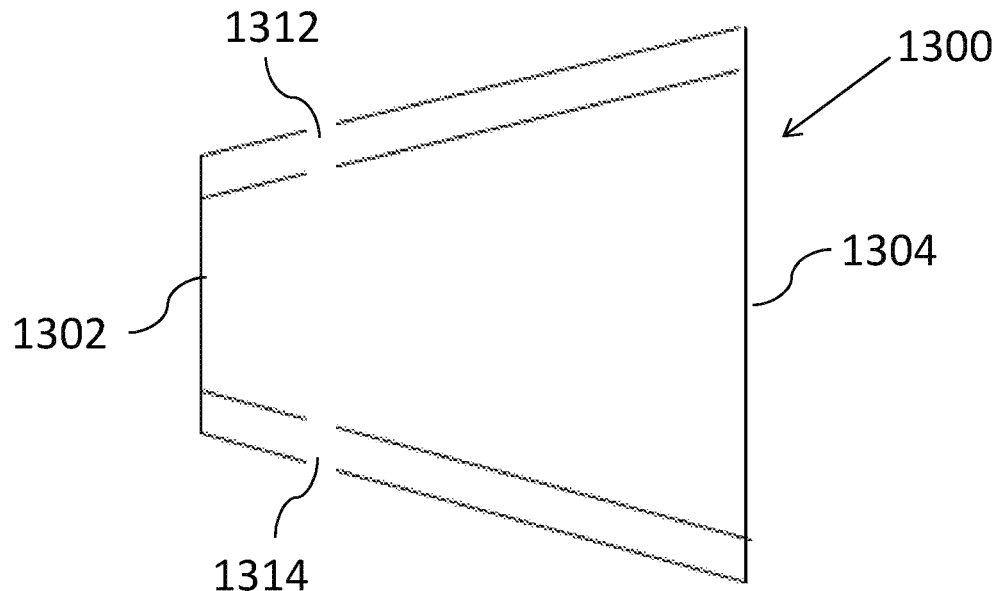
FIG. 13 is an illustration of an inner tube comprising microchannels in the same radial plane, in accordance with certain examples.
Figure 14:
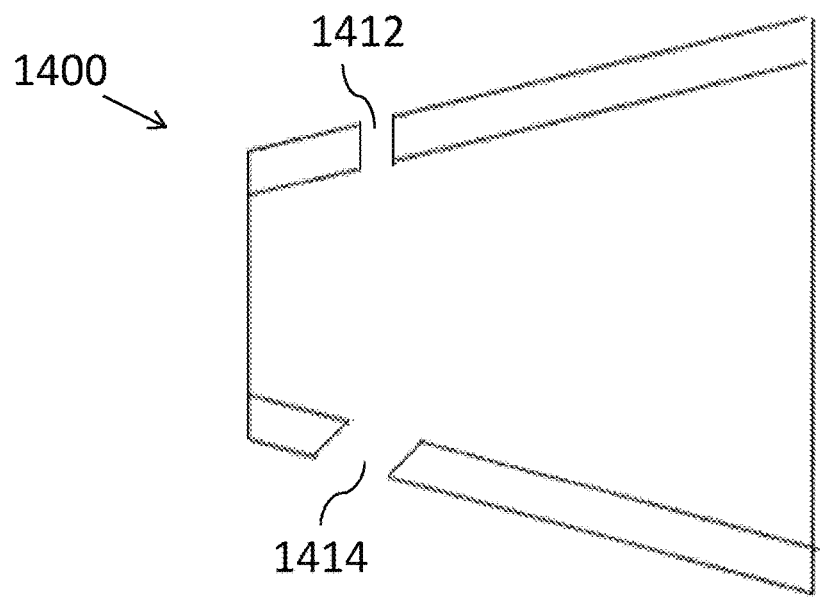
FIG. 14 is an illustration of an inner tube comprising differently sized microchannels, in accordance with certain configurations.
Figure 15:
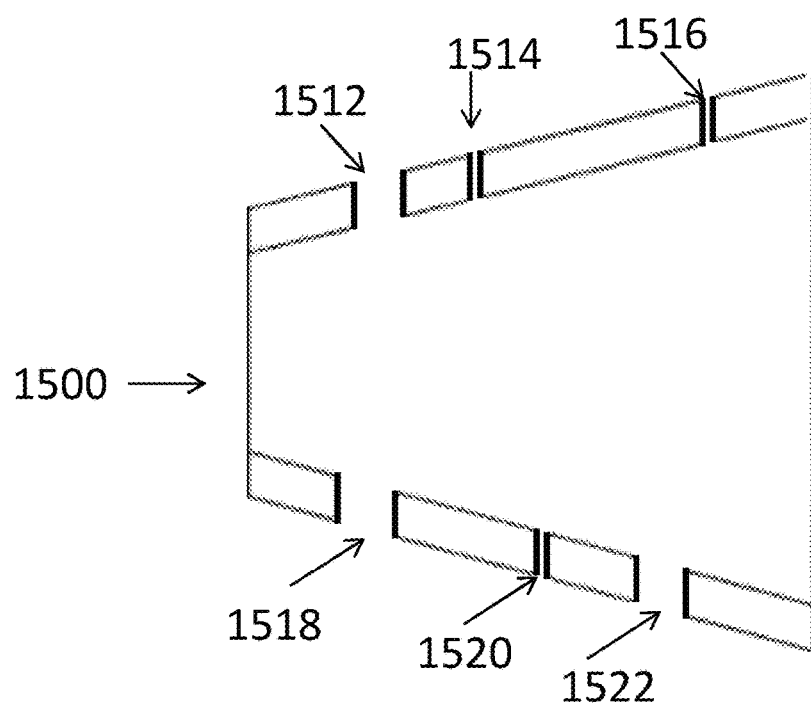
FIG. 15 is an illustration of an inner tube comprising a plurality of differently sized microchannels, in accordance with certain examples.

In certain configurations, the inner tube of the spray chamber may comprise one or more plurality of microchannels to permit a gas flow to flow from an external surface of the inner tube to an internal surface of the inner tube or vice versa or both. A cross section of one configuration is shown in FIG. 13. The inner tube 1300 comprises an inlet end 1302 and an outlet end 1304. Microchannels 1312, 1314 are shown as being positioned closer to the inlet end 1302, but this arrangement is not required. The microchannels 1312, 1314 are positioned in substantially the same radial plane, though they may be offset from each other if desired. For example, one of the microchannels 1312, 1314 can be positioned closer to the outlet end 1304 in a longitudinal direction of the inner tube 1300. In addition, the shape, orientation and/or diameter of the microchannels 1312, 1314 need not be the same. One illustration of differently sized microchannels is shown in FIG. 14. An inner tube 1400 comprises a first microchannel 1412 positioned substantially perpendicular to a longitudinal axis of the inner tube 1400 and a second microchannel 1414 positioned at an angle to the longitudinal axis of the inner tube 1400. In addition, the diameter of the microchannel 1414 is larger than the diameter of the microchannel 1412. In some instances, a plurality of individual microchannels can be positioned along a longitudinal direction of the inner tube. Referring to FIG. 15, an inner tube 1500 comprising a plurality of microchannels 1512-1522 is shown.

In certain embodiments, the spray chambers described herein can be used in combination with inductively coupled plasma mass spectrometry to measure single particles, single molecules or single cells. For example, it may be desirable to measure the levels of one or more metals in a single cell rather than measuring metal levels in a cell population. The spray chambers described herein can be used to select a single cell from a cell population and spray the single selected cell into the plasma. In some examples, this single cell selection permits the study of intrinsic metals, the uptake of dissolved (ionic) and nanoparticulate metals, chelated or complexed metals or other metals present in ionic or complexed forms within a cell. A single molecule or single cell can be delivered intact to the plasma, which can ionize any metals within the cell for analysis, e.g., using mass spectrometry, optical emission spectroscopy or atomic absorption spectroscopy. Ionization of the cell can product a burst of ions with the intensity of the resulting signal generally being proportional to the size of the particle and the number of pulses being related to the particle concentration. Rapid, continuous measurements can be performed to ensure single particle detection is accomplished and multiple different particles can be counted. Illustrative single particle inductively coupled plasma methods are described, for example, by Hineman A., Stephan C. *J. Anal. At. Spectrom.* 2014, 29, 152.

In certain examples, the exact nature of the cells used can vary from animal cells, plant cells, algae cells, fungal cells, bacterial cells, viruses or other cells. In some examples, the cells may be mammalian cells, e.g., human cells, or cells derived from mammalian cells. In some examples, the mammalian cells may be those cells which are derived from endoderm, ectoderm, or mesoderm progenitor cells. For example, the mammalian cells may be one or more of cells derives from endoderm including, but not limited to, a salivary gland mucous cell, a salivary gland number 1, Von Ebner's gland cell in tongue, a mammary gland cell, a lacrimal gland cell, a ceruminous gland cell in ear, an eccrine sweat glandering dark cell, an eccrine sweat gland clear cell, an apocrine sweat gland cell, a gland of Moll cell in eyelid, a sebaceous gland cell, a Bowman's gland cell in nose, a Brunner's gland cell in duodenum, a seminal vesicle cell, a prostate gland cell, a bulbourethral gland cell, a Bartholin's gland cell, a Gland of Littre cell, a uterus endometrium cell, a insolated goblet cell of respiratory and digestive tracts, a stomach lining mucous cell, a gastric gland zymogenic cell, a gastric gland oxyntic cell, a pancreatic acinar cell, a Paneth cell of small intestine, a Type II pneumocyte of lung, a club cell of lung, an anterior pituitary cell (somatotropes, lactotropes, thryotropes, gonadotropes, corticotropes), an intermediate pituitary cell, a secreting melanocyte-stimulating hormone, a magnocellular neurosecretory cells (nonsecreting oxytocin cell, a secreting vasopressin cell), gut and respiratory tract cells (secreting serotonin cell, secreting endorphin cell, secreting somatostatin cell, secreting gastrin cell, secreting secretin cell, nonsecreting cholecystokinin cell, secreting insulin cell, secreting glucagon cell, nonsecreting bombesin cell), thyroid gland cells (thyroid epithelial cell, parafollicular cell), parathyroid gland cells (parathyroid chief cell, oxyphil cell), adrenal gland cells (chromaffin cells, secreting steroid hormones (mineralocorticoids and gluco corticoids)), Leydig cell of testes secreting testosterone, Theca interna cell of ovarian follicle secreting estrogen, Corpus luteum cell of ruptured ovarian follicle secreting progesterone (Granulosa lutein cells, Theca lutein cells), Juxtaglomerular cell (renin secretion), Macula densa cell of kidney, Peripolar cell of kidney, Mesangial cell of kidney, pancreatic islets (islets of Langerhans) such as alpha cells (secreting glucagon), beta cells (secreting insulin and amylin), delta cells (secreting somatostatin), PP cells (gamma cells) (secreting pancreatic polypeptide), or Epsilon cells (secreting ghrelin). In other examples, the cells may be one or more of those derived from ectoderm including, but not limited to, keratinizing epithelial cells (Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell)), wet stratified barrier epithelial cells (surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts)), nerve cells or supporting nervous tissue cells, sensory transducer cells (Auditory inner hair cell of organ of Corti, Auditory outer hair cell of organ of Corti, Basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons (various types), Photoreceptor cells of retina in eye: Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons (various types), Touch-sensitive primary sensory neurons (various types), Type I carotid body cell (blood pH sensor), Type II carotid body cell (blood pH sensor), Type I hair cell of vestibular system of ear (acceleration and gravity), Type II hair cell of vestibular system of ear (acceleration and gravity), Type I taste bud cell), autonomic neuron cells (Cholinergic neural cell (various types), Adrenergic neural cell (various types), Peptidergic neural cell (various types)), Sense organ and peripheral neuron supporting cells (Inner pillar cell of organ of Corti, Outer pillar cell of organ of Corti, Inner phalangeal cell of organ of Corti, Outer phalangeal cell of organ of Corti Border cell of organ of Corti, Hensen cell of organ of Corti, Vestibular apparatus supporting cell, Taste bud supporting cell, Olfactory epithelium supporting cell, Schwann cell, Satellite glial cell (encapsulating peripheral nerve cell bodies), enteric glial cell), central nervous system neurons and glial cells such as neuron cells (Interneurons, Basket cells, Stellate cells, Golgi cells, Granule cells, Lugaro cells, Unipolar brush cells, Martinotti cells, Chandelier cells, Medium spiny neurons, Cajal-Retzius cells, Double-bouquet cells, Neurogliaform cells Spinal interneuron Renshaw cells, Principal cells Spindle neuron, Pyramidal cells Place cells Grid cells, Speed cells, Head direction cells, Betz cells, Stellate cells Boundary cells, Astrocyte (various types), Oligodendrocyte, Ependymal cells Tanycytes, Lens cells, Anterior lens epithelial cell and Crystallin-containing lens fiber cell. In additional examples, the cells may be one or more of those derived from mesoderm including, but not limited to, adipocytes, White fat cell, Brown fat cell, a Liver lipocyte, a barrier function cells (lung, gut, exocrine glands and urogenital tract), kidney cells, Kidney parietal cell, Kidney glomerulus podocyte, Kidney proximal tubule brush border cell, Loop of Henle thin segment cell, Kidney distal tubule cell, Kidney collecting duct cell Principal cells, Intercalated cells, Type I pneumocyte (lining air space of lung cell), Pancreatic duct cell (centroacinar cell), Nonstriated duct cell (of sweat gland, salivary gland, mammary gland, etc.) Principal cell Intercalated cell, Duct cell (of seminal vesicle, prostate gland, etc.), Intestinal brush border cell (with microvilli), Exocrine gland striated duct cell, Gall bladder epithelial cell, Ductulus efferens nonciliated cell, Epididymal principal cell, Epididymal basal cell, Endothelial cells, Ameloblast epithelial cell (tooth enamel secretion), Planum semilunatum epithelial cell of vestibular system of ear (proteoglycan secretion), Organ of Corti interdental epithelial cell (secreting tectorial membrane covering hair cells), Loose connective tissue fibroblasts, Corneal fibroblasts (corneal keratocytes), Tendon fibroblasts, Bone marrow reticular tissue fibroblasts, Other nonepithelial fibroblasts, Pericyte, Nucleus pulposus cell of intervertebral disc, Cementoblast/cementocyte (tooth root bonelike ewan cell secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), Pancreatic stelle cell, a Skeletal muscle cell, Red skeletal muscle cell, White skeletal muscle cell, Intermediate skeletal muscle cell, Nuclear bag cell of muscle spindle, Nuclear chain cell of muscle spindle, a satellite cell (stem cell), Heart muscle cells Ordinary heart muscle cell, Nodal heart muscle cell, Purkinje fiber cell, Smooth muscle cell (various types), Myoepithelial cell of iris, Myoepithelial cell of exocrine glands, Erythrocyte (red blood cell), Megakaryocyte (platelet precursor), Monocyte (white blood cell), Connective tissue macrophage (various types) Epidermal Langerhans cell, Osteoclast (in bone), Dendritic cell (in lymphoid tissues) Microglial cell (in central nervous system), Neutrophil granulocyte, Eosinophil granulocyte Basophil granulocyte, Hybridoma cell, Mast cell, Helper T cell, Suppressor T cell, Cytotoxic T cell, Natural killer T cell, B cell, Natural killer cell, Reticulocyte, Stem cells and committed progenitors for the blood and immune system (various types), germ cells, Oogonium/ Oocyte, Spermatid, Spermatocyte, Spermatogonium cell (stem cell for spermatocyte), Spermatozoon, Nurse cell, Ovarian follicle cell, Sertoli cell (in testis), Thymus epithelial cell, Interstitial cells or Interstitial kidney cells.

In certain examples, the spray chambers described herein can be used to select and analyze inorganic and/organic species within a single cell. For example, a cell population can be introduced into a spray chamber, and the spray chamber can be used to select a single cell from the introduced cell population. The selected cell can be sprayed into an ionization device to ionize/atomize inorganic or organic species in the sprayed, selected single cell. At least one inorganic or organic species in the sprayed, selected single cell can be detected. As noted herein, the selected cell can be many different types of cells including animal cells, plant cells, algae cells, fungal cells, bacterial cells, viruses or other cells. In some examples, the selected cell from the cell population is mammalian cell derived from endoderm, ectoderm or mesoderm. In other examples, at least one metal species in the selected, single cell is detected. In some examples, at least one amino acid, peptide or protein in the selected, single cell is detected. In other examples, at least one lipid, fatty acid, fat, etc. in the selected, single cell is detected. In some examples, at least one monosaccharide, disaccharide, polysaccharide or carbohydrate in the selected, single cell is detected. In other examples, at least one nucleotide, nucleic acid, e.g., deoxyribonucleic acid, ribonucleic acid, etc. in the selected, single cell is detected. In other instances, a level of an external agent, e.g., a cancer drug, steroid or other pharmacological or biological agent taken up by the selected single cell is detected. In some examples, the presence or absence of a biological agent, e.g., an antibody such as a monoclonal antibody, bound to or associated with the selected, single cell is detected.

In other examples, a method comprises providing one or more spray chambers as described herein, and providing instructions for using the provided spray chamber to select the single cell from the cell population and to detect at least one inorganic or organic species in the selected, single cell using an ionization device. For examples, the method comprises providing instructions for using the spray chamber with an inductively coupled mass spectrometer to detect the at least one inorganic or organic species in the selected, single cell. In some examples, the method comprises providing instructions for using the spray chamber with an inductively coupled optical emission spectrometer to detect the at least one inorganic or organic species in the selected, single cell. In other examples, the method comprises providing instructions for using the spray chamber with an inductively coupled atomic absorption spectrometer to detect the at least one inorganic or organic species in the selected, single cell. In some examples, the method comprises providing instructions for using a mammalian cell population to select a single mammalian cell.

Certain specific examples are described below to illustrate some of the components and aspects of the spray chambers described herein.

Example 1

Figure 16:
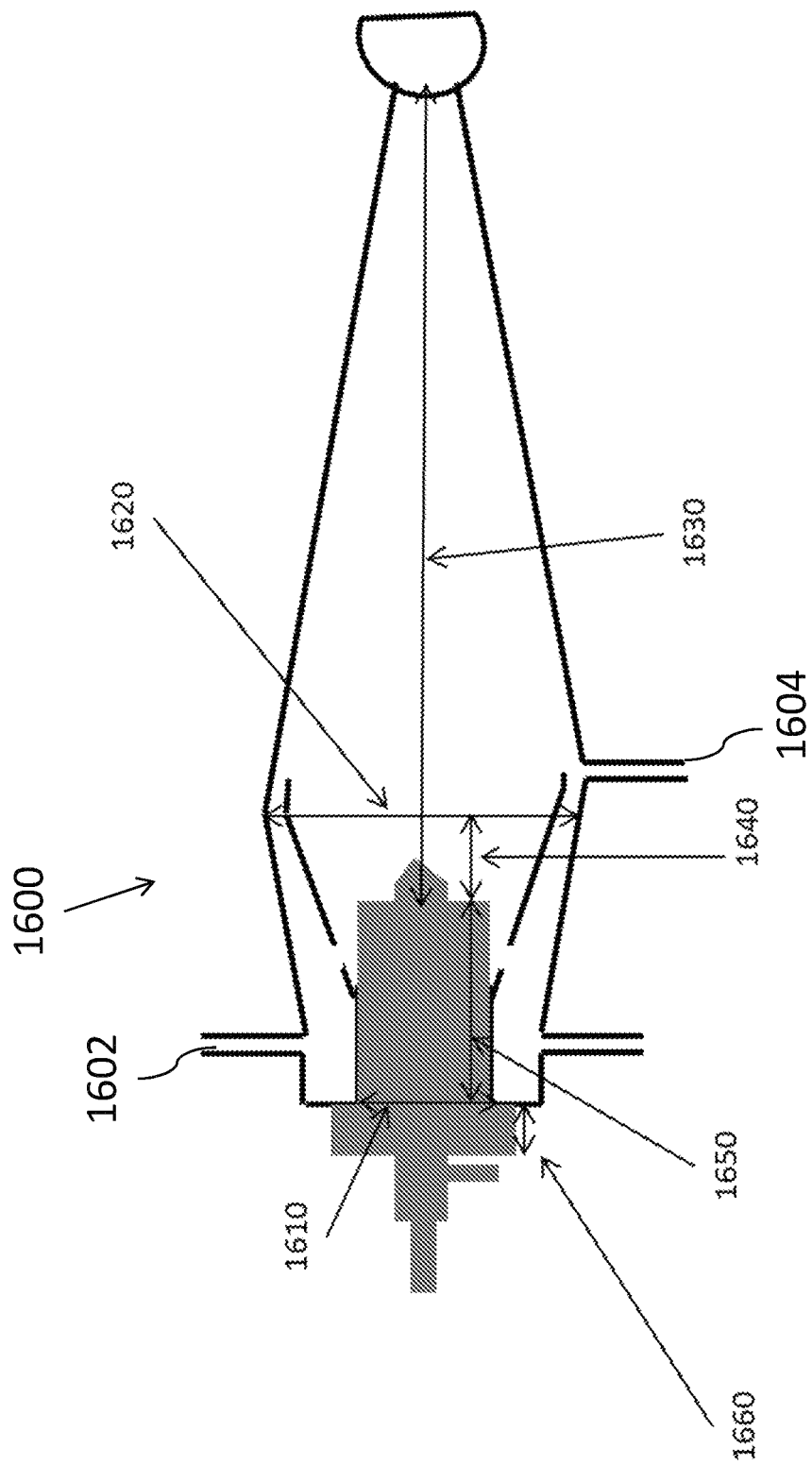
FIG. 16 is an illustration showing certain dimensions of a spray chamber, in accordance with certain configurations.
Figure 17:
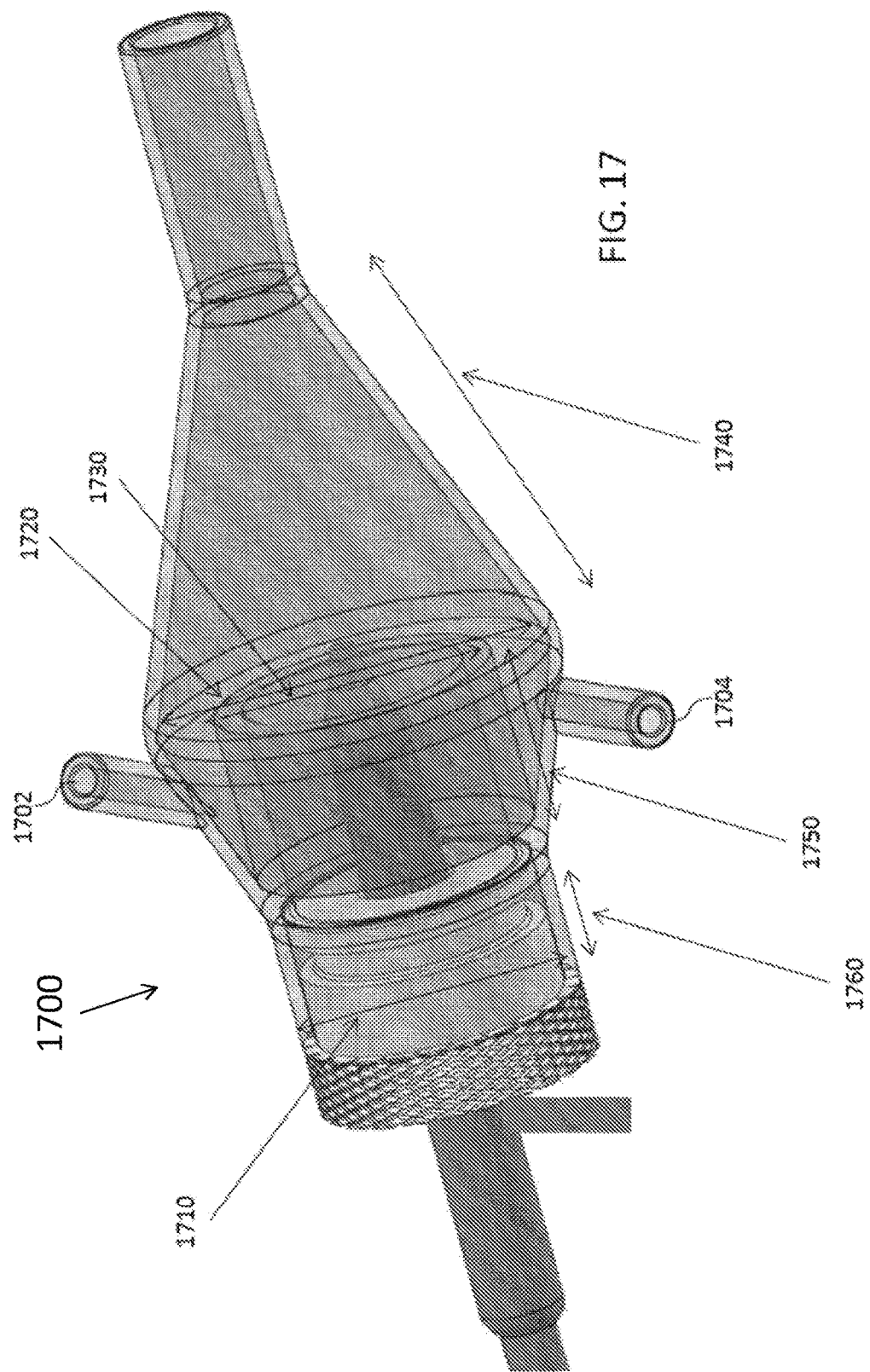
FIG. 17 is an illustration showing certain dimensions of another spray chamber, in accordance with certain configurations.
Figure 18:
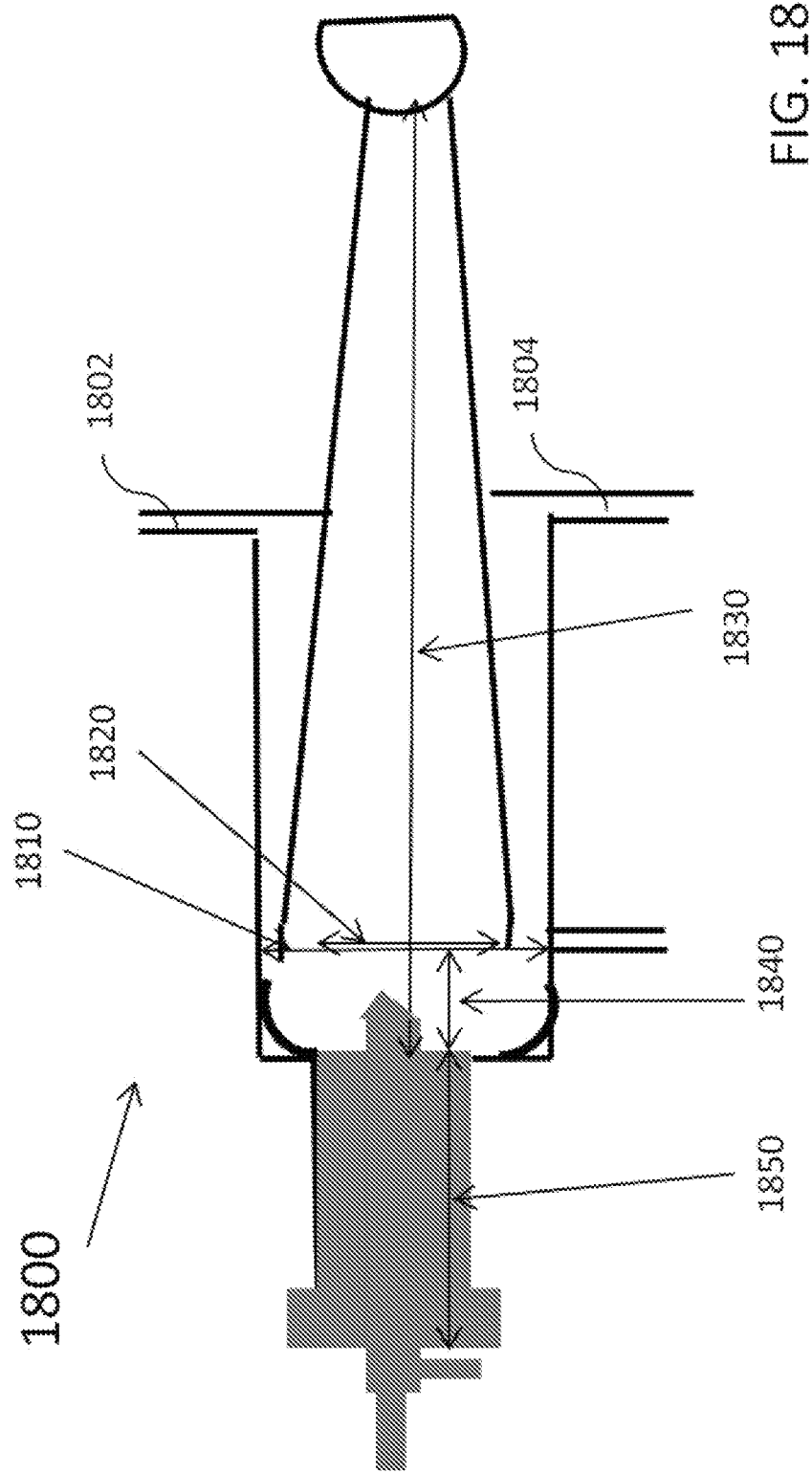
FIG. 18 is an illustration showing certain dimensions of an additional spray chamber, in accordance with certain configurations.

A spray chamber similar to that shown in FIG. 2 is shown in FIG. 16. The dimensions of the various components are shown using the arrows provided on FIG. 16. A dimension 1610 is about 1.5 cm, a dimension 1620 is about 3 cm, a dimension 1630 is about 13 cm, a dimension 1640 is about 1.5 cm, a dimension 1650 is about 2.2 cm and a dimension 1660 is about 1 cm. The spray chamber 1600 has dual makeup gas inlets 1602, 1604, and an inner tube with a plurality of microchannels. The dual makeup gas inlets are fluidically coupled to a makeup gas source (not shown) to provide tangential gas flows within the spray chamber 1600. Laminar flow is created by positioning the inner tube suitably in the spray chamber 1600. The laminar flow acts to shield the outer tube or chamber from droplet deposition. Gas flows through the microchannels of the inner tube acts to prevent droplet formation on the inner tube. The gas flows together can be used to select single particles or single cells from a sample.

Example 2

A spray chamber similar to that shown in FIG. 3 is shown in FIG. 17. The dimensions of the various components are shown using the arrows provided on FIG. 17. A dimension 1710 is about 1.5 cm, a dimension 1720 is about 3 cm, a dimension 1730 is about 2.5 cm, a dimension 1740 is about 11 cm, a dimension 1650 is about 1.5 cm and a dimension 1760 is about 1.5 cm. The spray chamber 1700 has dual makeup gas inlets 1702, 1704, and an inner tube with a plurality of microchannels. The dual makeup gas inlets are fluidically coupled to a makeup gas source (not shown) to provide tangential gas flows within the spray chamber 1700. Laminar flow is created by positioning the inner tube suitably in the spray chamber 1700. The laminar flow acts to shield the outer tube or chamber from droplet deposition. Gas flows through the microchannels of the inner tube acts to prevent droplet formation on the inner tube. The gas flows together can be used to select single particles or single cells from a sample.

Example 3

A spray chamber similar to that shown in FIG. 4 is shown in FIG. 18. The dimensions of the various components are shown using the arrows provided on FIG. 18. A dimension 1810 is about 3 cm, a dimension 1820 is about 2.5 cm, a dimension 1830 is about 13.5 cm, a dimension 1840 is about 1 cm, and a dimension 1850 is about 3.2 cm. The spray chamber 1800 has dual makeup gas inlets 1802, 1804, and an inner tube with a plurality of microchannels. The dual makeup gas inlets are fluidically coupled to a makeup gas source (not shown) to provide tangential gas flows within the spray chamber 1800. Laminar flow is created by positioning the inner tube suitably in the spray chamber 1800. The laminar flow acts to shield the outer tube or chamber from droplet deposition. Gas flows through the microchannels of the inner tube acts to prevent droplet formation on the inner tube. The gas flows together can be used to select single particles or single cells from a sample.

Example 4

A cell suspension can be nebulized by introducing the cell suspension through a nebulizer fluidically coupled to a spray chamber as described herein. The spray chamber can select individual cells and provide them to an inductively coupled plasma. As each cell enters the plasma, it is ionized, and the resulting ion burst from the intrinsic metal species is detected by a mass spectrometer. Each cell is treated the same as an individual particle. Cell concentrations can desirably be around 100,000 cell/mL to minimize coincidence—a situation where to cells are provided at the same time to the plasma.

To determine the effectiveness of detection of cisplatin using single cell ICP-MS using the spray chambers described herein, an ovarian cancer cell line (CP70) was exposed to cisplatin and monitored over time. Analyses were carried out on a PerkinElmer NexION 350 D ICP-MS with a 2 mm quartz injector and quartz torch operating with an RF power of 1600 W. A spray chamber as shown in FIG. 2 (though the spray chambers of FIGS. 3, 4 and 5A-5D could be used instead) can be used with a high efficiency concentric glass nebulizer (Meinhard) was used with the spray chamber and the NexION 350 D instrument.

Figure 19:
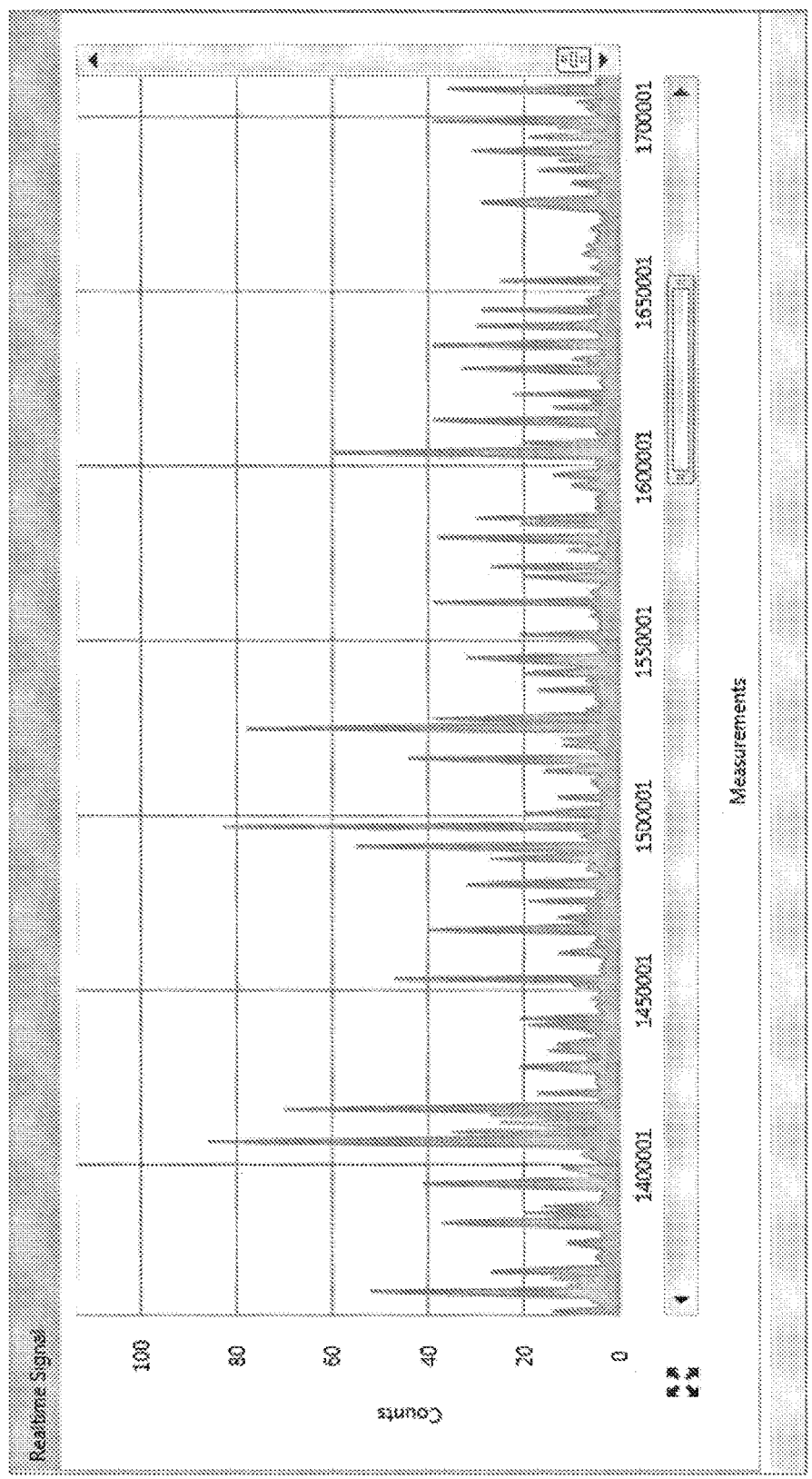
FIG. 19 is a graph showing the raw ICP-MS signal of the cisplatin-exposed cells where the 195Pt isotope was monitored, in accordance with certain examples.

FIG. 19 shows the raw ICP-MS signal of the cisplatin-exposed cells where the 195Pt isotope was monitored. Because background levels of Pt are non-existent and there are no common interferences on 195Pt, each spike represents Pt detected in an individual cell. Using an analysis time of one minute and a dwell time of 50 microseconds, a total of 1.2 million data points were collected in FIG. 19. The variation in peak size reflects the information that we are seeking in this technique: an insight into the uptake mechanism as various cells will have different amounts of intrinsic Pt, all dependent on the molecular mechanism that is occurring and their ability to uptake and store Pt.

Figure 20:
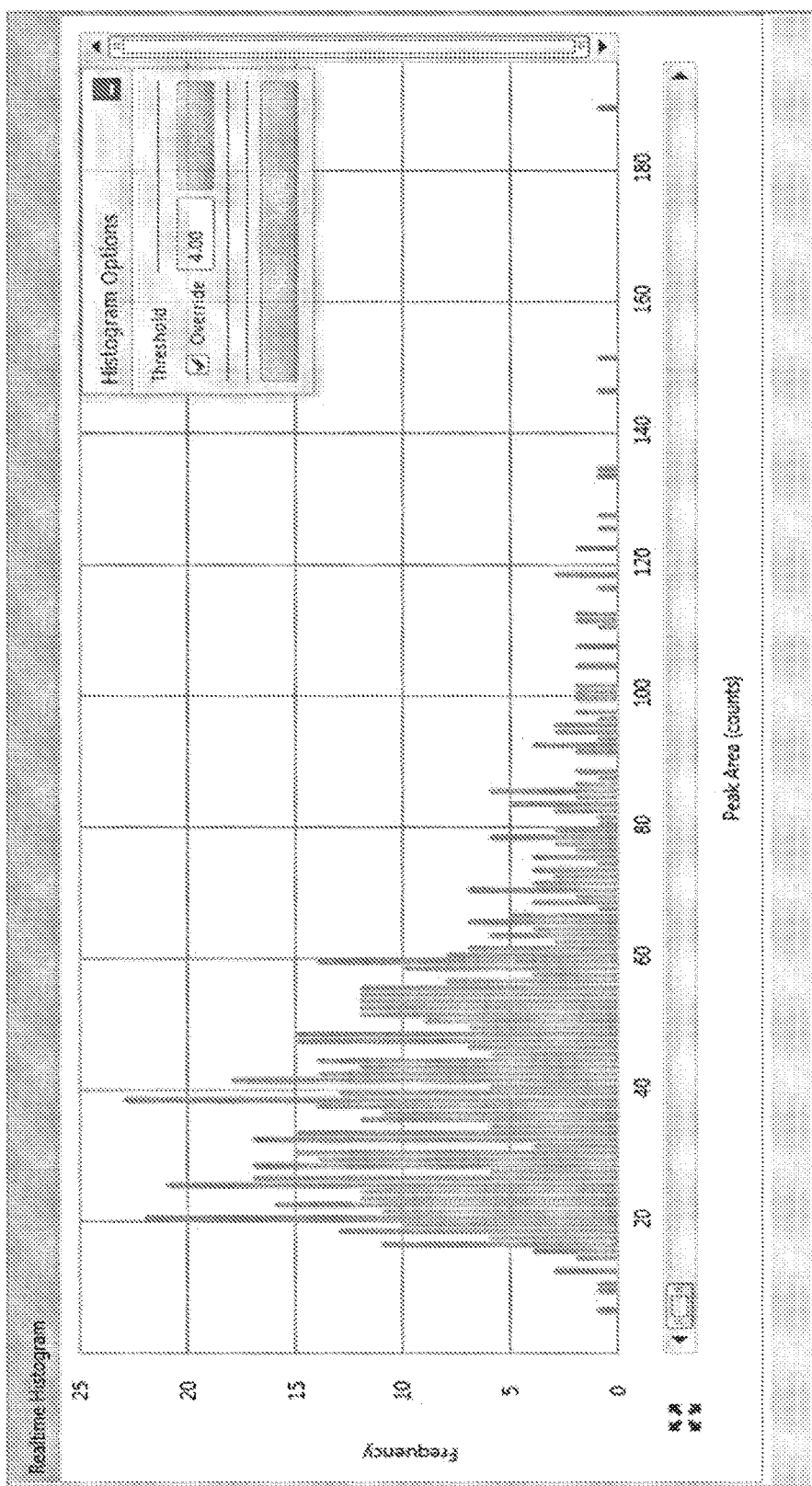
FIG. 20 shows Pt content distribution in CP70 after being exposed to cisplatin for four hours.
Figure 21:
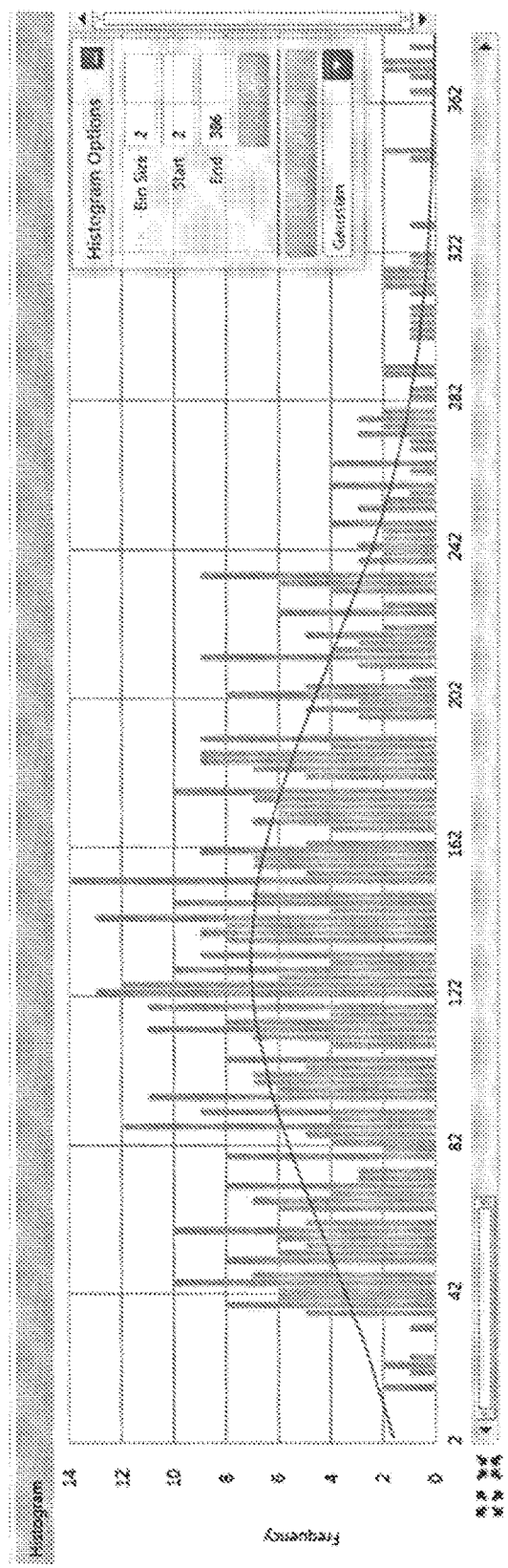
FIG. 21 shows uptake tracking of Pt by CP70 ovarian cancer cells over the course of eight hours.

FIG. 20 shows Pt content distribution in CP70 after being exposed to cisplatin for four hours. FIG. 21 shows the ability of the technique to track the uptake of Pt by CP70 ovarian cancer cells over the course of eight hours. FIG. 21 shows that the Pt content within cells increases over time, signifying increased cisplatin uptake, which is represented with the shift to the right in the distribution.

Figure 22:
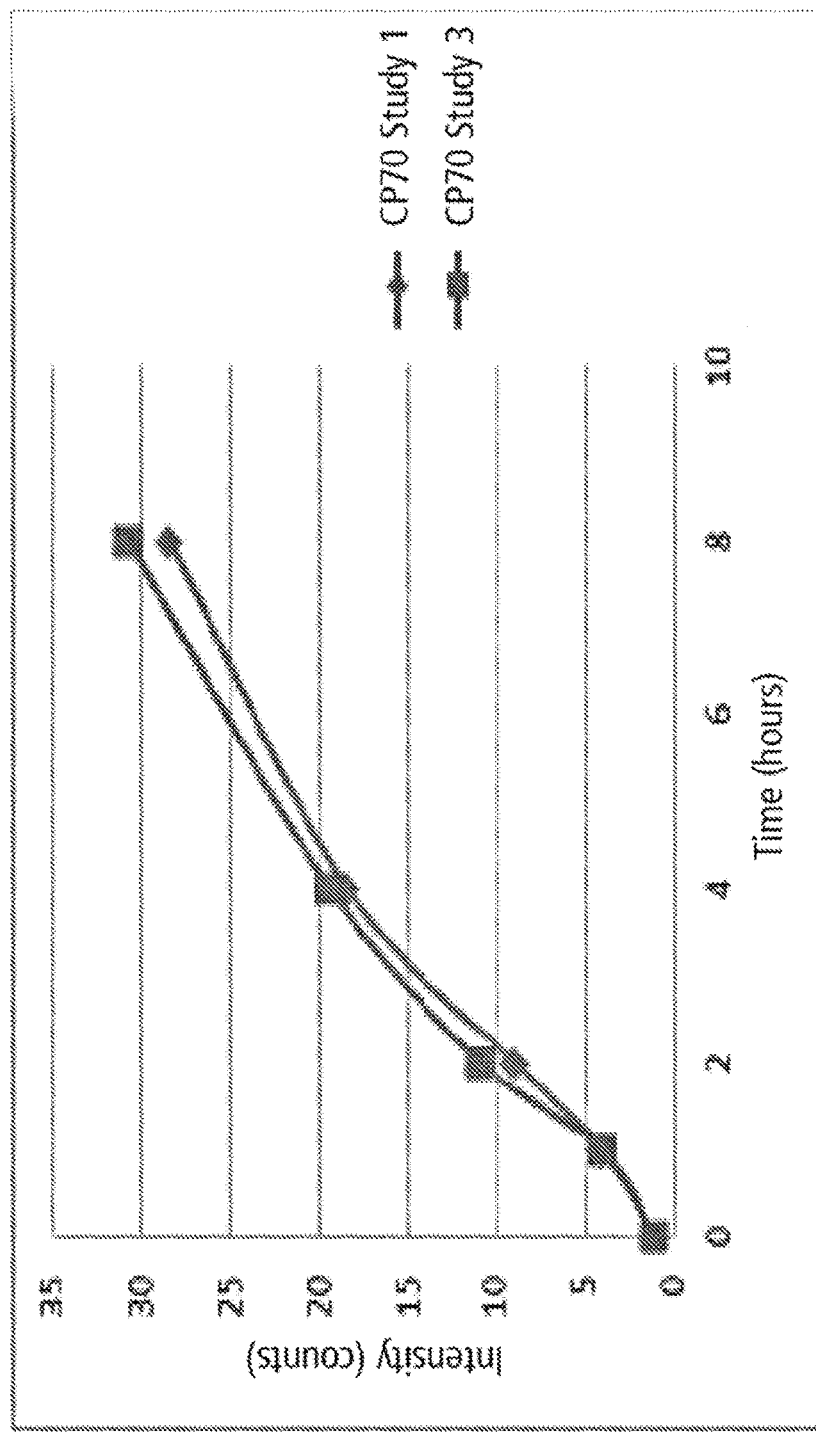
FIG. 22 shows the average Pt content vs. exposure time.

The average Pt content vs. exposure time was repeated on two non-consecutive days and shows the great precision and reproducibility of using the spray chambers described herein to detect single cell species (FIG. 22).

Example 5

Nanoparticles (NPs) are being used in a wide variety of applications, from improving the quality of various consumer products to enhancing cancer research. Like every chemical, there is a potential risk associated with the release of NPs into the environment. As a traditional remedy against infections, silver's alleged curative powers are now marketed as NP additives in a host of consumer antimicrobial products ranging from socks that fight odors to stuffed animals for children that fend off germs. At the same time, research studies conclusively show the toxicity of nanosilver on cells.

Figure 23:
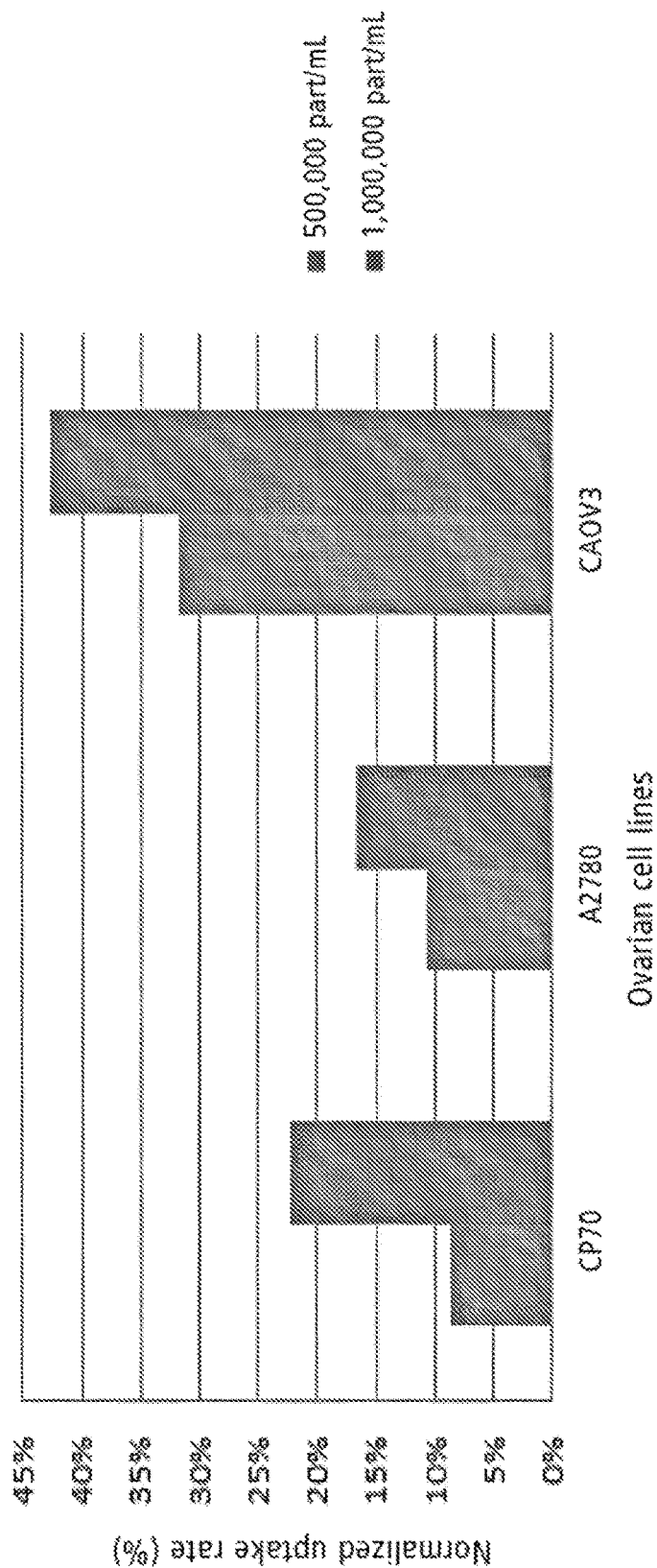
FIG. 23 shows uptake of two different gold NP concentrations by different cell lines.

Three different lines of ovarian cells were exposed to two different gold NP concentrations. The cells were washed to remove excess NPs and then analyzed after 21 hours to determine the cellular content. The data in FIG. 23 shows that different cell lines have different NP uptake rates, which may be dependent, to a certain extent, on the NP concentrations studied. 500,000 parts/mL is shown on the left side of each bar grouping, and 1,000,000 parts/mL is shown on the right side of each bar grouping.

Example 6

Figure 24:
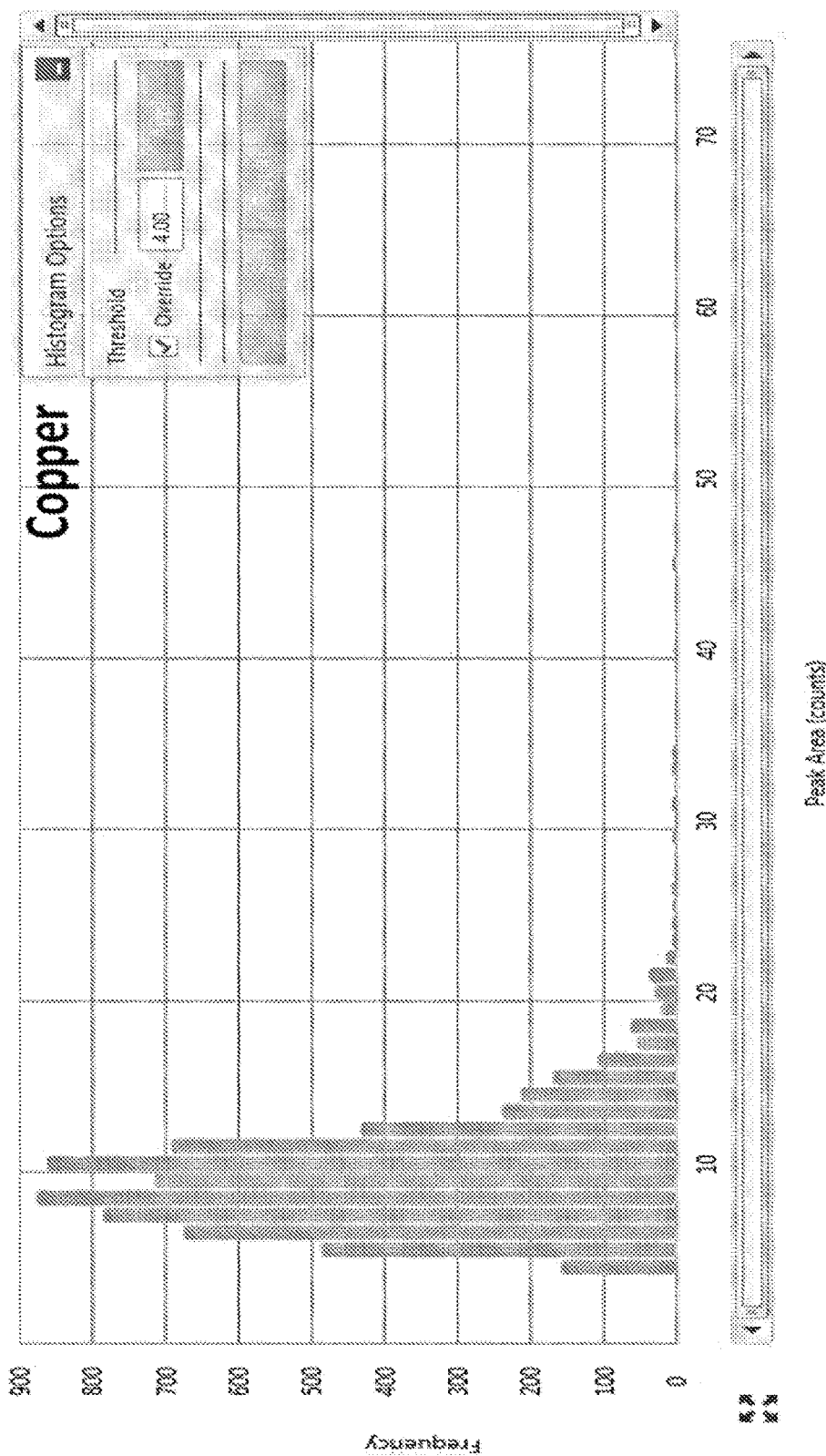
FIG. 24 shows measurement of copper.
Figure 25:
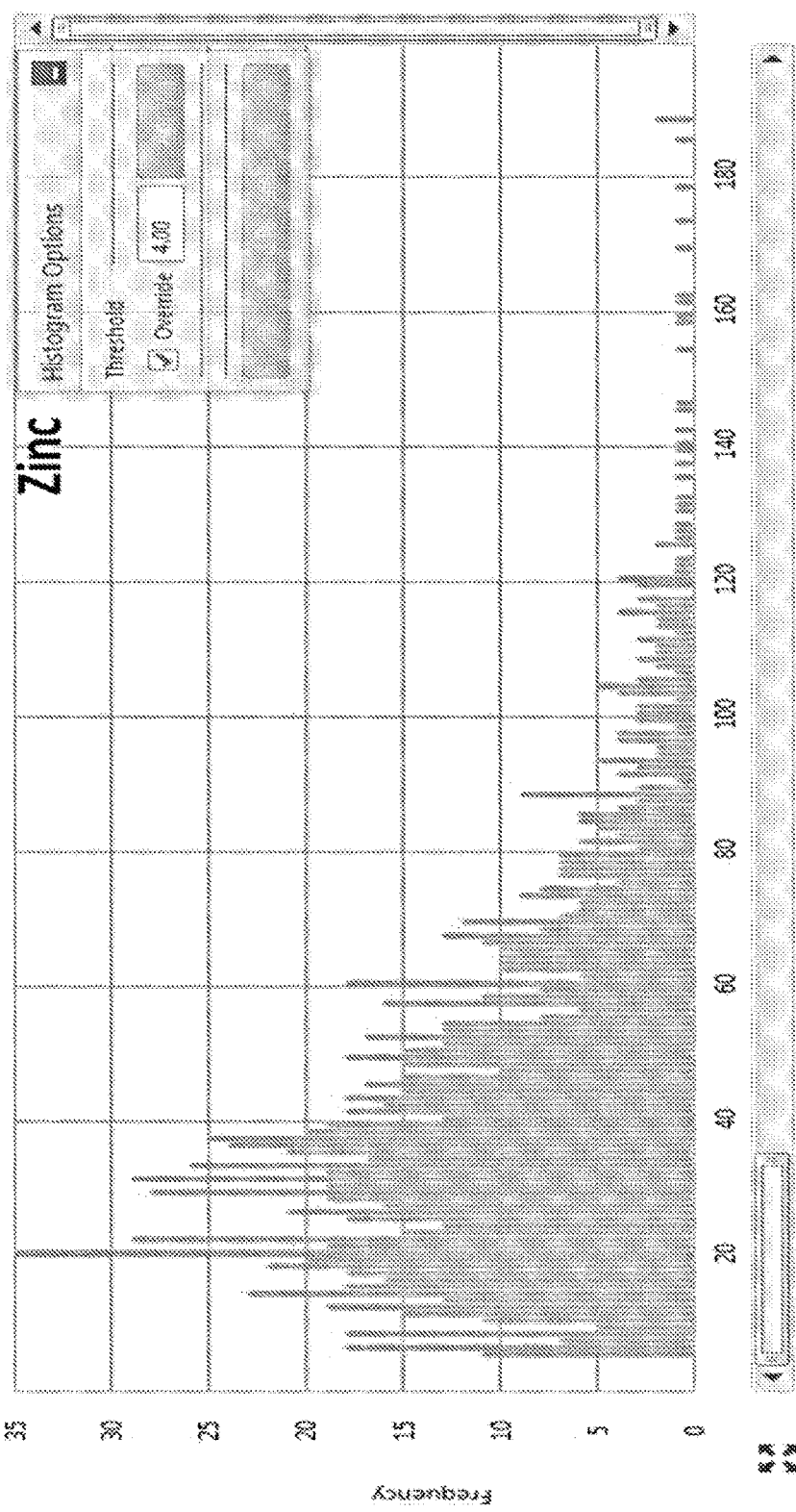
FIG. 25 shows measurement of zinc in individual cells from the CP70 ovarian cancer cell line.

The spray chambers described herein can also be used to determine the intrinsic metal content of the cells themselves in their natural environment without any prior exposure. The metal of interest may be present in the culture solution in which the cells are suspended and is responsible for the background level. If the background is high, it may obscure the metal signal from the cells. FIGS. 24 and 25 shows measurement of copper (FIG. 24) and zinc (FIG. 25) in individual cells from the CP70 ovarian cancer cell line.

Example 7

The uptake of nanoparticle and ionic/dissolved gold by fresh water algae was determined using single cell ICP-MS. The uptake of metals into individual cells is of interest to both environmental and human health studies, whether the metal is dissolved or exists as nanoparticles (NPs). Currently, cellular metal content is studied by removing the cells from their culture media (either by centrifugation or filtration), washing with fresh media solution, and then acid-digesting them for analysis by ICP-MS4. This methodology gives the total metal or particle content in a given number of cells rather than on a per-cell basis. As such, the metal concentration of an individual cell relies on the assumption that all cells accumulate the same amount of ionic or nanoparticulate metal. This assumption is not always true, as demonstrated by techniques such as transmission electron microscope (TEM), scanning electron microscope (SEM), and fluorescent tracking. These microscopy techniques allow visualization of NP uptake into cells but are time consuming and prone to artifacts. TEM and SEM are qualitative, and labelling may give false positives where the label-NP complexes are not persistent.

Algae cell cultures were prepared at concentrations of 200,000 cells/mL and exposed to either ionic gold or gold NPs (60 nm NPs, NIST 8013) at various concentrations including 1, 2 or 3 ppb ionic gold, 200,000 parts/mL, 400,000 parts/mL or 600,000 parts/mL gold NPs. Each exposure study was run in triplicate at 20° C. for up to 74 hours with a light:dark cycle of 12 hours light and 12 hours dark. During the exposure, 1 mL aliquots were removed periodically for analysis. Prior to analysis, the cells were separated from the exposure media and washed with media three times. Each wash cycle consisted of centrifuging the cells for 15 minutes at 300 g-force and re-suspended in 1 mL of fresh culture media (containing no NP or ionic Au). After the three washes, the cell recovery was 43.8±8.6%.

All analyses were carried out on a PerkinElmer NexION® ICP-MS using the Syngistix™ Single Cell Application Software Module for data collection and processing. The instrumental conditions used were: sample uptake rate of 0.03-0.04 mL/minute, a 2.0 mm id quartz injector, a RF power of 1600 Watts, a nebulizer gas flow rate of 0.36 L/minute, and a makeup gas flow rate of 0.7 Liters/minute. A spray chamber as shown in FIG. 2 (though the spray chambers of FIGS. 3, 4 and 5A-5D could be used instead) can be used with a Meinhard HEN nebulizer. Since cells are typically larger than the aerosol droplets which are passed to the plasma, a conventional spray chamber limits their transport to the plasma.

Calibrations were performed with both ionic/dissolved and NP standards. The ionic calibrations were performed with 1, 2, and 3 ppb gold, while the NP calibrations used 10, 30, and 60 nm gold NPs (NIST 8011, 8012, and 8013, respectively), prepared at 50,000 part/mL. All standards were prepared in the algae media to matrix-match the cell suspensions. Transport efficiency was determined using the 60 nm gold NPs.

Before analyzing the cells for gold NP uptake, the effect of Au on the cells themselves must be determined. This was accomplished by exposing cells to different concentrations of ionic/dissolved gold and different concentrations of gold NPs. The cell concentrations were then monitored over 74 hours using a hemocytometer. As shown in FIGS. 26A and 26B, there was no significant difference in cell concentration between the exposed and control cells for both the ionic (FIG. 26A) and NP (FIG. 26B) gold exposures. As a result, gold does not impact cell concentrations.

Figure 27:
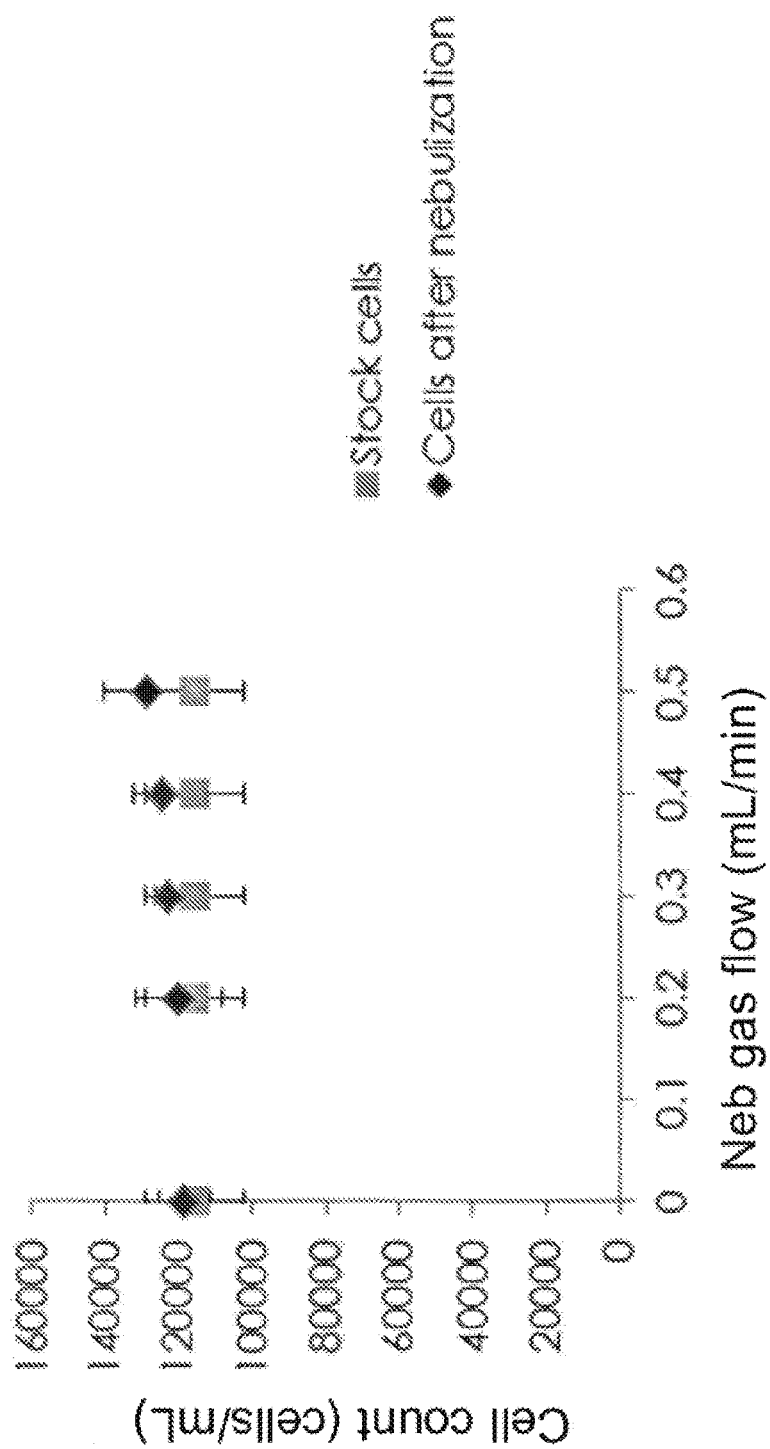
FIG. 27 is a graph of cell counts vs nebulizer gas flow, in accordance with certain examples.
Figures 28A, 28B, 28C, 28D:
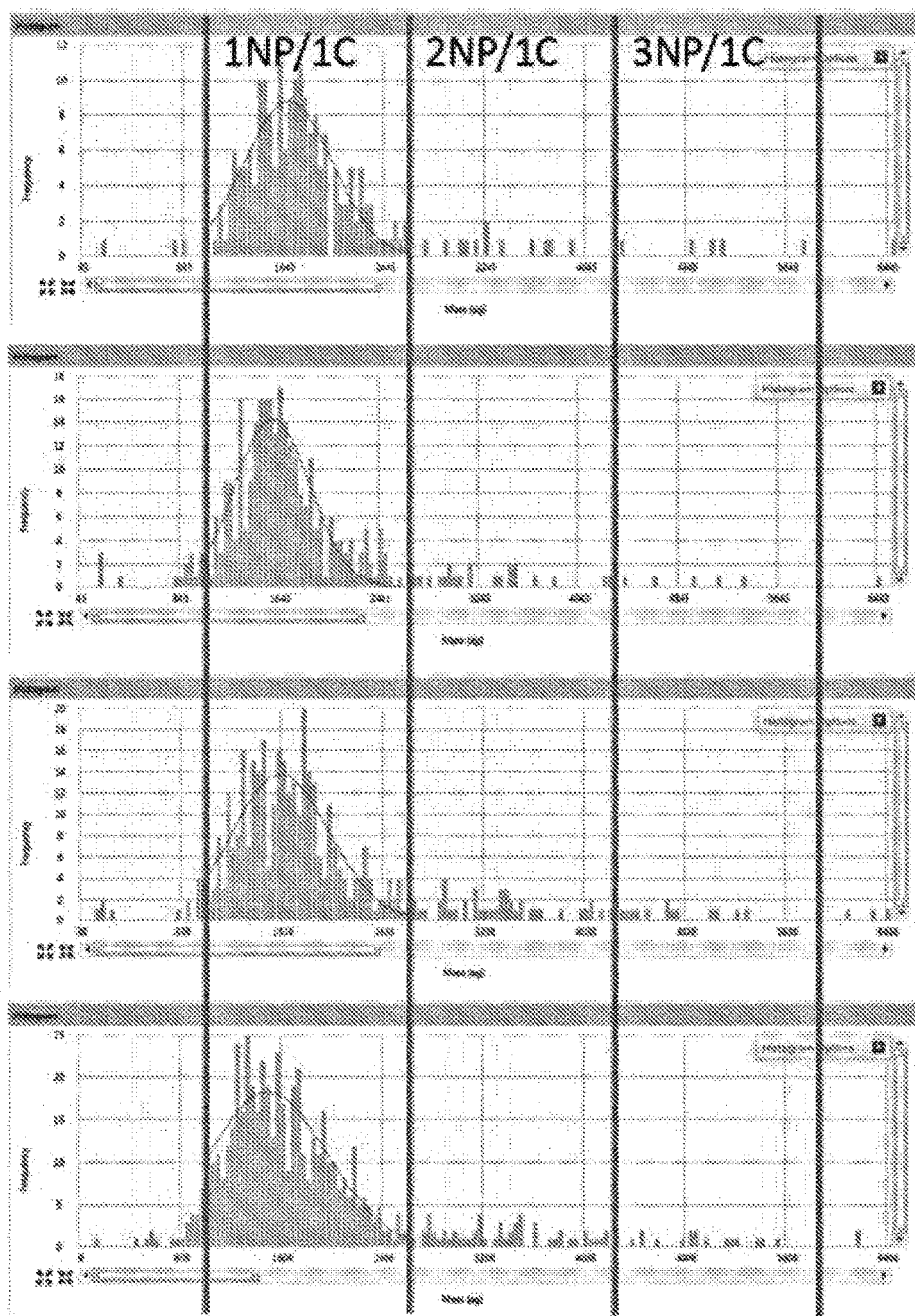
FIGS. 28A, 28B, 28C and 28D show nanoparticle uptake at different exposure times.

The cell line used in this study is *Cyptomonas ovata*, which has a size range of 20-30 microns. The aspiration of the cells through the nebulizer can subject them to high pressures, which are dependent on the nebulizer, sample flow rate, and nebulizer gas flow. To ensure that the cells were not damaged during nebulization, a variety of sample uptake and nebulizer gas flow rates were evaluated by counting the cells before and after the nebulization process using light microscopy. FIG. 27 shows that 100% of the cells were intact at a sample flow rate of 100 microliters/minute with a nebulizer gas flow of up to 0.5 mL/min. Therefore, under the selected instrument conditions, all of the cells should enter the spray chamber fully intact.

It is important to confirm that the signal measured from the washed cells is due to the metal within the cells themselves and not from residual metal left over from the original exposure. Thus, it is important to know that no NPs persist in the cell media after the final wash cycle. To check this, the cells were washed three times with fresh media. To monitor the NP content of the media, the supernatant of each cellular wash cycle was analyzed by SC-ICP-MS. The NP content was found to decrease over the three wash cycles, and zero particles were detected after the third wash.

One of the main advantages of SC-ICP-MS is the ability to determine not just the number of cells that contain NPs, but also the percentage of those cells which contain single or multiple NPs. In FIGS. 28A-28D there is a main peak around 1700 ag which is due to a single NP within the cells (labeled 1NP/1C≡1 particle/1 cell). The signal collected from cells showing the increase of cells containing gold metal over 74 hours along with an increase of cells containing more than one particle. Exposure times of 2 hours (FIG. 28A), 28 hours (FIG. 28B), 53 hours (FIG. 28C), and 74 hours (FIG. 28D). 1NP/1C=1 NP per cell; 2NP/1C=2 NPs per cell; 3NP/1C=3 NPs per cell. Since a single 60 nm Au NP corresponds to ≈1800 ag (as discussed earlier), then a mass of about 1700 ag gold measured from a cell corresponds to a single 60 nm gold NP in the cell. This slight reduction in mass is believed to result from the NP being within the cell, which will be explored by microscopy in a future study. As the exposure time increases from two hours (FIG. 28A) to 74 hours (FIG. 28D), the presence of multiple NPs per cell can be seen as peaks appearing at 3400 ag (2 NPs) and 5200 ag (3 NP), marked as 2NP/1C and 3NP/1C in A-C, respectively. With the ability to determine the number of NPs per cell, the percentage of cells containing various numbers of NPs can be tracked over time and as a function of the NP concentration in the algae media. As the exposure time increases, the number of cells with 1 NP increases, as would be expected. Also, a higher percentage of cells contain a single NP as the concentration of NPs in the media increases from 200,000 to 600,000 parts/mL. A similar trend is seen in the number of cells containing 2 NPs and 3 NPs in the 600,000 part/mL exposure. However, with the 200,000 part/mL, the number of cells that have taken up two or more nanoparticles is too small to draw any conclusions with regard to the effect of exposure time on uptake rate.

Figure 29A:
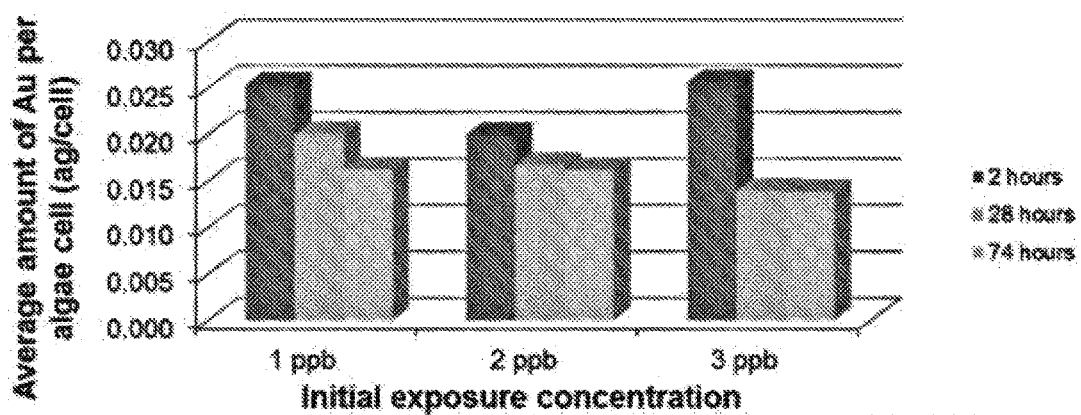
FIGS. 29A and 29B show gold uptake by algae cells, in accordance with certain embodiments.
Figure 29B:
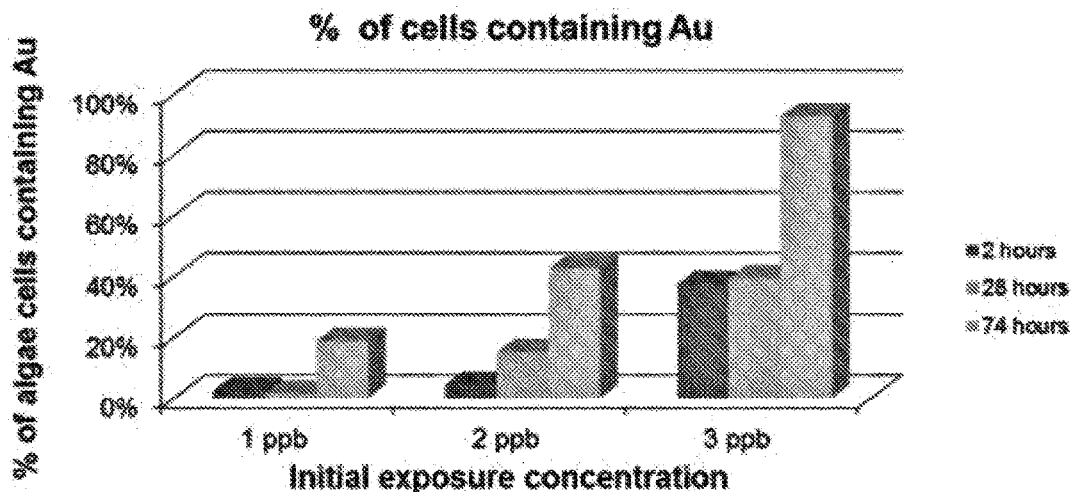

To determine the cellular uptake of ionic gold, algae cells were exposed to dissolved gold concentrations of 1, 2, and 3 micrograms/L for up to 74 hours, with sample aliquots being drawn at 2, 28, and 74 hours. As shown in FIG. 29A, there is an apparent decrease in the average amount of gold per cell (expressed as ag/cell) over time, which is independent of initial gold concentration. From left to right in each bar grouping of FIG. 29A, the ordering is 2 hours, 28 hours and 74 hours. However, as demonstrated in FIG. 29B, the percentage of cells containing gold increases over time and with initial Au exposure concentration. From left to right in each bar grouping of FIG. 29B, the ordering is 2 hours, 28 hours and 74 hours. These data suggest that there is a cellular mechanism that limits the amount of gold taken into the cell, which is dependent on the gold concentration in the cellular media.

Example 8

Cisplatin, carboplatin, and oxaliplatin are the most widely used of platinum-based cancer chemotherapy drugs in the Western world. Cisplatin's effectiveness is due to its ability to bind to the DNA, resulting in DNA-platinum (Pt) adducts, which bend the DNA. The cells must then repair the DNA damage, otherwise DNA replication is blocked resulting in cell death1.

Many cancers are initially sensitive to platinum-based treatment, but patients frequently relapse with tumors displaying resistance to further cisplatin therapy. Cisplatin drug resistance is due to three major molecular mechanisms: increased DNA repair, increased cytosolic inactivation, and altered cellular accumulation. Decreased cellular uptake or increased cellular export of cisplatin constitutes the mechanisms involved in altered cellular accumulation.

Cisplatin uptake in two ovarian cancer cell lines was evaluated using single particle ICP-MS (SP-ICP-MS). The ovarian cancer cell lines A2780 and A2780/CP70 were used in all experiments. Cells were grown in RPMI 1641 media (Gibco™) supplemented with 10% fetal bovine serum (FBS, Gibco™), insulin (Sigma-Aldrich™), 1-glutamine (Gibco™), and pen/strep (Gibco™) under 5% $CO_2$ at 37° C. For serum starvation experiments, cells were plated and allowed to attach to the dishes. The media was removed and replaced with serum-free media for approximately 18 hours after which the media was replaced with regular media to begin cisplatin treatment. Cisplatin was re-suspended at 1 mg/mL in sterile saline and vigorously shaken for 30 minutes prior to treatment. Cells were treated with 30 μM cisplatin for a time course where samples were collected at 1, 2, 4, and 8 hours post-treatment. For analysis, cells were washed twice with phosphate-buffered saline (PBS) and collected using the non-enzymatic cell dissociation solution Cellstripper (Corning™). Cells were centrifuged at 500×g for 10 minutes. The supernatant was discarded, and the cells were resuspended in 1 mL PBS, filtered through a 70 μm nylon mesh, and quantitated by hemocytometer counting. Cells were diluted in PBS to a final concentration of 100,000 cells/mL and kept on ice until injection.

Analyses were performed with PerkinElmer's NexION® ICP-MS using the Syngistix™ Single Cell Application Software Module for data collection and processing. Instrumental conditions were as follows: sample uptake rate 0.04 mL/minute, 2.0 mm id quartz injector, 1600 Watts RF power, 0.36 L/minute nebulizer gas flow rate, 0.7 L/minute makeup gas flow rate, and a 60 second sample analysis time. A Meinhard HEN nebulizer and the spray chamber of FIG. 2 were also used (though the spray chambers of FIGS. 3, 4 and 5A-5D could be used instead). The Single Cell Sample Introduction Kit (Part No. N8150031) was used for sample introduction to the NexION. The kit consists of a high-efficiency nebulizer (Part No. N8142046) and the spray chamber designed for transport of cells to the plasma. Cells (1-100 microns) are larger than droplets which typically pass through conventional spray chambers (less than 2 microns).

Ionic platinum standards were prepared in PBS to matrix match the cell sample. A standard curve was generated using 1, 2, and 3 ppb platinum standard. Transport efficiency was determined using 60 micron gold nanoparticles in PBS.

Figure 30A:
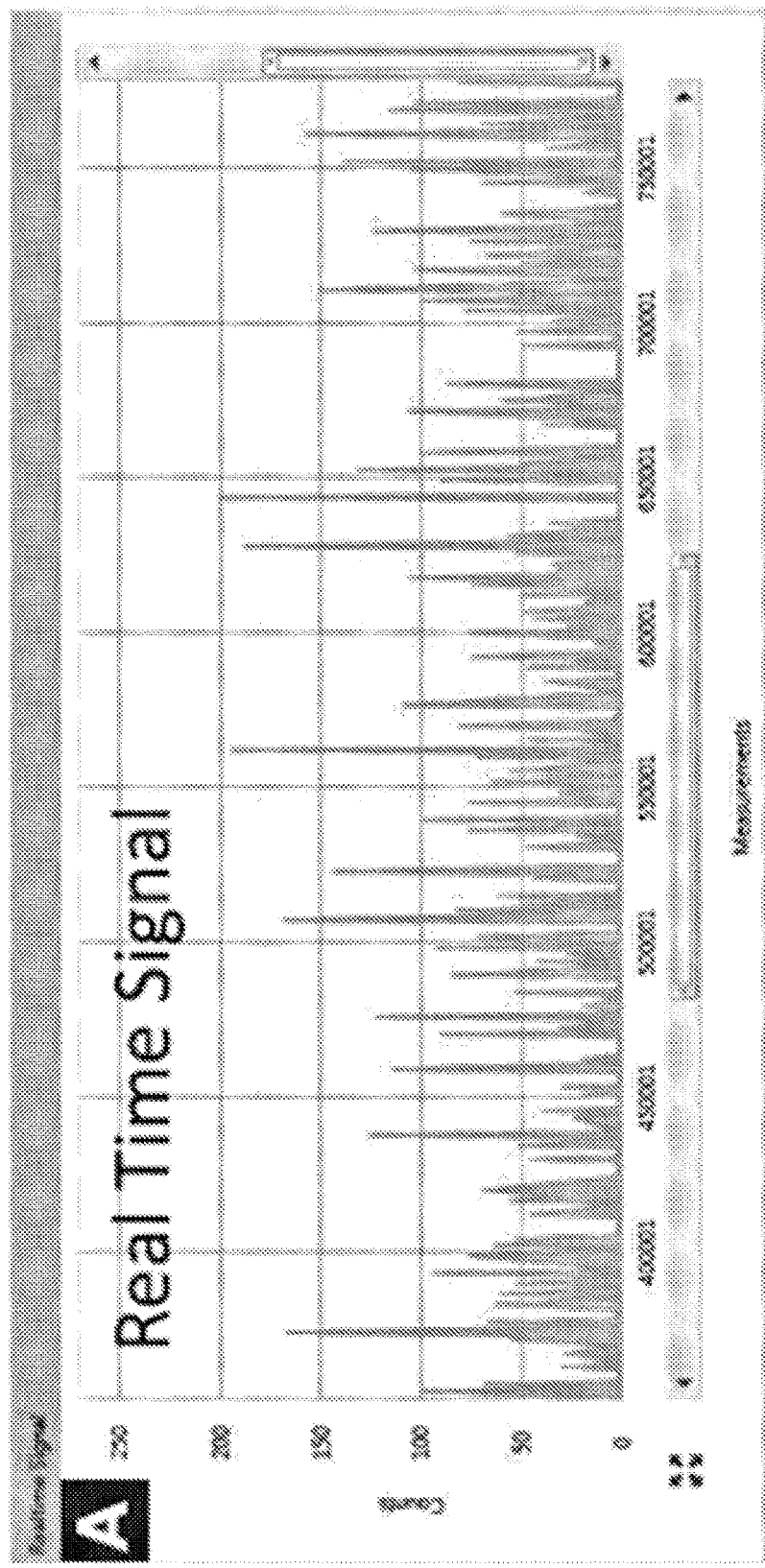
FIGS. 30A, 30B and 30C are graphs showing counts vs measurements (FIG. 30A) representing the real time signal, frequency vs peak area (counts) representing the real time histogram (FIG. 30B), and integration of the mass distribution peak (FIG. 30C)
Figure 30B:
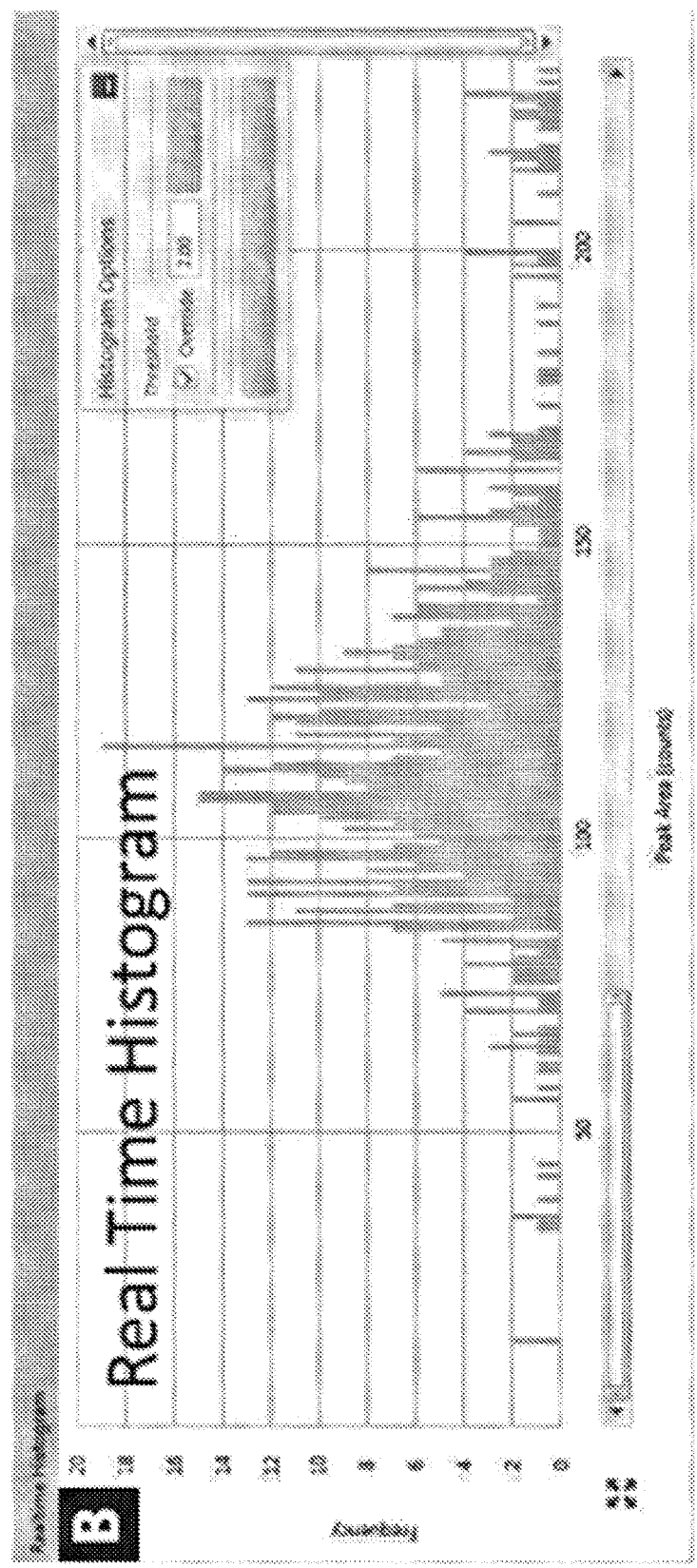
Figure 30C:
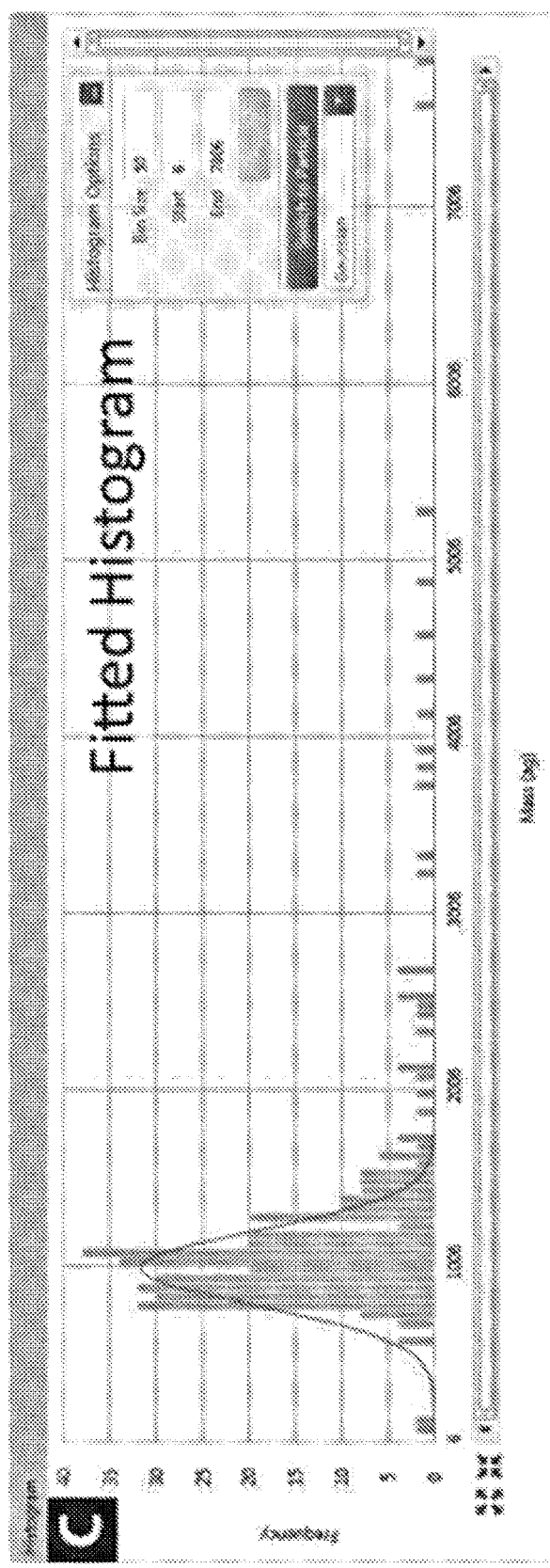

The cells chosen for this study are the ovarian cancer cell lines A2780 and A2780/CP70, which are good models for developing the single cell method since the molecular mechanism for resistance is altered by cisplatin uptake. A2780 is a cisplatin-sensitive cell line, while the A2780/CP70 line is cisplatin resistant. This resistance was developed by exposing the A2780 parental cell line to increasing doses of cisplatin. The A2780/CP70 cells developed resistance by reducing cisplatin uptake in addition to up-regulating DNA repair. We explored cisplatin uptake by performing a time course experiment to analyze how the distribution of cisplatin uptake changed over time within the cellular population. Both cell lines were treated for 1, 2, 4, and 8 hours with 30 µM cisplatin. During sample analysis, two real-time plots are produced: one shows the intensity response vs. sample number, while the second takes this data and converts it to a histogram showing the frequency of response vs. mass-per-cell; both plots are shown in FIGS. 30A and 30B with FIG. 30A (counts vs measurements) representing the real time signal, FIG. 30B (frequency vs peak area (counts)) representing the real time histogram. After the data is collected, the mass distribution peak can be integrated, as shown in FIG. 30C (frequency vs mass(ag)).

The cisplatin time course results are shown in FIGS. 31A-31D and 32A-32D. FIG. 31A represents the A2780 cells at 1 hour exposure, FIG. 31B represents the A2780 cells at 2 hours exposure, FIG. 31C represents the A2780 cells at 4 hours exposure, and FIG. 31D represents the A2780 cells at 4 hours exposure. FIG. 32A represents the A2780/CP70 cells at 1 hour exposure, FIG. 32B represents the A2780/CP70 cells at 2 hours exposure, FIG. 32C represents the A2780/CP70 cells at 4 hours exposure, and FIG. 32D represents the A2780/CP70 cells at 4 hours exposure. The y-axis for each graph represents frequency and the x-axis represents mass (ag).

At one hour of cisplatin treatment, both cell lines show very little uptake of platinum. As time progresses, cells from both lines import increasing amounts of cisplatin and show a heterogeneous distribution. At eight hours post cisplatin treatment, the A2780 and A2780/CP70 cell lines have a subpopulation of cells with less cisplatin in comparison to the rest of the cellular population. Additionally, there is a significant difference between the cell lines at eight hours as A2780 has an increased population of cells with more cisplatin than A2780/CP70.

Figure 33:
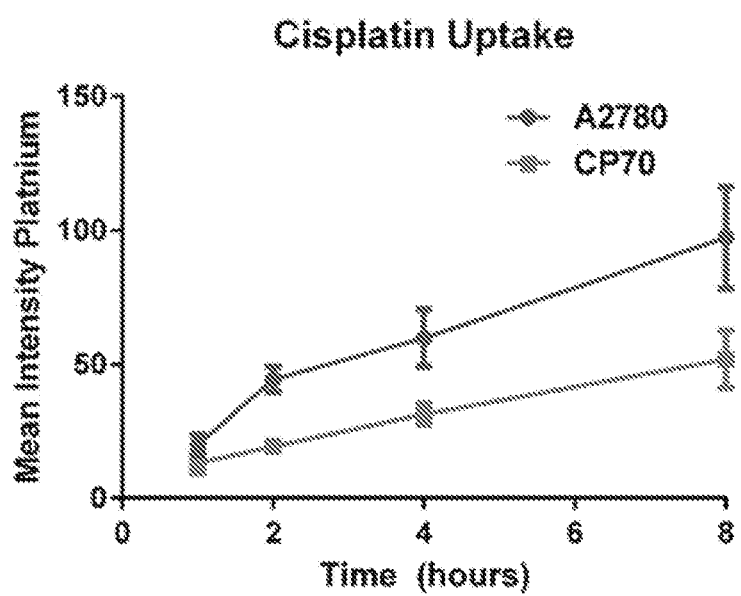
FIG. 33 is a graph showing cisplatin uptake difference in two cell lines.

The time course data was summarized by fitting each histogram with a Log Normal curve. The mean intensity was determined for each time point and plotted to show the cisplatin uptake difference between A2780 and A2780/CP70 cells over time, as shown in FIG. 33. It was observed that cisplatin-sensitive A2780 cells have increased cisplatin uptake in comparison to the cisplatin-resistant A2780/CP70 cells over time.

To determine whether the heterogeneous distribution of cisplatin uptake was due to differences in the cell cycle, cells were serum starved. When cells are grown in tissue culture, the culture is typically a mixture of asynchronous cells growing at different rates, resulting in a variety of cells at different stages of the cell cycle. The four parts of the cell cycle are referred to as G1, S, G2, and M. The G1 phase is the first (and typically longest) growth phase, followed by the S phase, where DNA is synthesized and replicated in preparation for cell division. The G2 growth phase is next, followed by the M (or mitosis) phase where cells divide into two cells. Thus, it is plausible that the differences in cisplatin levels may be due to differences in the cell cycle phases. By starving the cells of serum, the growth factors are removed from the media and the cells will stall in the G1 phase.

The cisplatin uptake time experiments were repeated comparing the uptake difference between the serum-starved and control cells. FIGS. 34A and 34B show the results of the serum starvation experiments where the mean intensity was determined for each time point and plotted. These results show that serum starvation had no effect on the uptake of cisplatin in either the A2780 or the A2780/CP70 cell lines; both show similar cisplatin uptake rates as the control cells. Thus, these results suggest that the heterogeneous distribution of cisplatin uptake in cells is not due to the cell cycle but rather some other unknown mechanism.

Example 9

Figure 35:
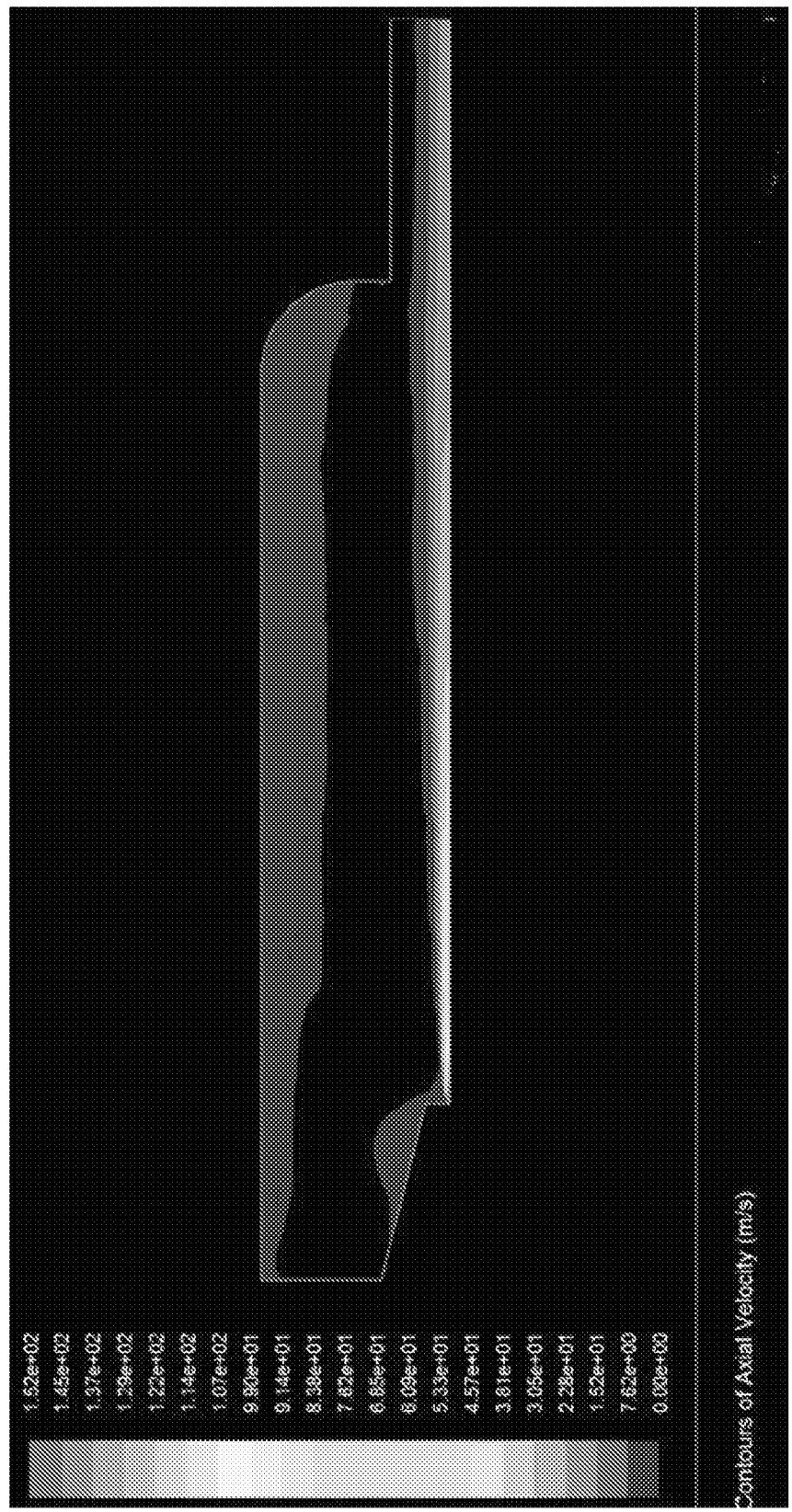
FIG. 35 is a simulation showing gas flow axial velocity in a forward direction of a spray chamber, in accordance with certain configurations.

A flow simulation was performed using the spray chamber shown in FIGS. 5A-5D using a computational fluid dynamics simulation. FIG. 35 shows the results of the simulation. FIG. 35 shows a gas flow axial velocity in a forward direction (a direction away from a nebulizer tip). The droplets are confined to the tangential flows and remain away from the inner surfaces of the outer chamber.

When introducing elements of the examples disclosed herein, the articles "a," "an," "the" and "said" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of analyzing inorganic or organic species in single cells in a cell population, the method comprising:
introducing a cell population into a spray chamber configured to couple to a nebulizer at an inlet end to receive a liquid sample from the nebulizer and provide an aerosolized sample spray at an outlet end to an ionization device, the spray chamber comprising an outer chamber comprising the inlet end, the outlet end and dual makeup gas inlet ports each configured to receive a gas to provide a tangential gas flow within the outer chamber, and an inner tube within the outer chamber, the inner tube comprising a plurality of internal microchannels configured to receive makeup gas introduced into the outer chamber from the dual makeup gas inlets, wherein the inner tube is sized and arranged to provide a laminar flow between an outer surface of the inner tube and an inner surface of the outer chamber to reduce droplet deposition on the inner tube;

selecting a single cell from the introduced cell population;

spraying the selected single cell from the spray chamber and into an ionization device to analyze the inorganic or organic species in the selected single cell; and detecting at least one inorganic or organic species in the sprayed, selected single cell.

2. The method of claim 1, further comprising selecting the cell population to be a mammalian cell derived from endoderm.

3. The method of claim 1, further comprising selecting the cell population to be a mammalian cell derived from ectoderm.

4. The method of claim 1, further comprising selecting the cell population to be a mammalian cell derived from mesoderm.

5. The method of claim 1, further comprising detecting at least one metal species in the selected, single cell.

6. The method of claim 1, further comprising detecting at least one protein in the selected, single cell.

7. The method of claim 1, further comprising detecting at least one lipid in the selected, single cell.

8. The method of claim 1, further comprising detecting at least one carbohydrate in the selected, single cell.

9. The method of claim 1, further comprising detecting at least one nucleic acid in the selected, single cell.

10. The method of claim 1, further comprising detecting a level of an external agent taken up by the selected single cell.

11. The method of claim 1, further comprising configuring the ionization device to be an inductively coupled plasma.

12. The method of claim 1, further comprising detecting the inorganic or organic species from the selected, single cell that has been sprayed into the ionization device using a mass spectrometer.

13. The method of claim 12, further comprising detecting the inorganic or organic species from the selected, single cell that has been sprayed into the ionization device using optical emission spectroscopy.

14. The method of claim 12, further comprising detecting the inorganic or organic species from the selected, single cell that has been sprayed into the ionization device using atomic absorption spectroscopy.

15. The method of claim 12, further comprising configuring the ionization device as a torch and an induction coil, a torch and an induction coil comprising a radial fin, or a torch and an at least one flat plate electrode.

* * * * *

UNITED STATES PATENT AND TRADEMARK OFFICE
CERTIFICATE OF CORRECTION

PATENT NO.         : 10,395,912 B2
APPLICATION NO.    : 16/146752
DATED              : August 27, 2019
INVENTOR(S)        : Chady Stephan et al.

Page 1 of 1

It is certified that error appears in the above-identified patent and that said Letters Patent is hereby corrected as shown below:

In the Claims

Column 28, Line 14, (approx.) in Claim 13, delete "The method of claim 12" and insert --The method of claim 1--

Column 28, Line 18, (approx.) in Claim 14, delete "The method of claim 12" and insert --The method of claim 1--

Column 28, Line 22, (approx.) in Claim 15, delete "The method of claim 12" and insert --The method of claim 1--

Signed and Sealed this
Seventh Day of April, 2020

Andrei Iancu
*Director of the United States Patent and Trademark Office*